USOO5728385A

United States Patent [19]
Classen

[11] Patent Number: 5,728,385
[45] Date of Patent: Mar. 17, 1998

[54] METHOD AND COMPOSITION FOR AN EARLY VACCINE TO PROTECT AGAINST BOTH COMMON INFECTIOUS DISEASES AND CHRONIC IMMUNE MEDIATED DISORDERS OR THEIR SEQUELAE

[75] Inventor: John Barthelow Classen, Baltimore, Md.

[73] Assignee: Classen Immunotherapies, Inc., Baltimore, Md.

[21] Appl. No.: 104,529

[22] Filed: Aug. 12, 1993

[51] Int. Cl.[6] .................. A61K 39/02; A61K 39/12; A61K 39/116; A61K 39/295

[52] U.S. Cl. .................. 424/201.1; 424/184.1; 424/202.1; 424/203.1; 424/212.1; 424/217.1; 424/218.1; 424/219.1; 424/224.1; 424/227.1; 424/228.1; 424/230.1; 424/233.1; 424/234.1; 424/244.1; 424/245.1; 424/246.1; 424/247.1; 424/249.1; 424/254.1; 424/258.1; 424/261.1

[58] Field of Search .................. 424/88, 184.1, 424/201.1, 202.1, 203.1, 212.1, 217.1, 218.1, 219.1, 224.1, 227.1, 228.1, 230.1, 233.1, 234.1, 244.1, 245.1, 246.1, 247.1, 249.1, 254.1, 258.1, 261.1

[56] References Cited

U.S. PATENT DOCUMENTS

| 4,152,415 | 5/1979 | Harris et al. ................ 424/16 |
| 4,625,015 | 11/1986 | Green et al. ................ 530/324 |
| 4,695,459 | 9/1987 | Lawrence et al. ................ 424/95 |
| 4,710,380 | 12/1987 | Arthur ................ 424/101 |
| 4,857,318 | 8/1989 | Lee ................ 242/92 |
| 4,894,332 | 1/1990 | Schaller et al. ................ 435/69.3 |
| 5,151,023 | 9/1992 | Kuzuhara et al. ................ 424/89 |
| 5,254,340 | 10/1993 | Van Leengoed et al. ................ 424/92 |

FOREIGN PATENT DOCUMENTS

| 0343480 | 5/1989 | European Pat. Off. . |
| 8912455 | 12/1989 | WIPO . |
| 9010449 | 9/1990 | WIPO . |
| 9200755 | 1/1992 | WIPO . |

OTHER PUBLICATIONS

Baraff et al. "Immunologic Response to Early and Routine DTP Immunization in Infants", *Pediatrics*, 37–42 (Jan. 1984).

Barrett et al. "Multiple Antigen for Immunization Against Poliomyelitis, Diphtheria, Pertussis, and Tetanus" *JAMA*, 167:1103–1107 (Jun. 28, 1958).

Barrett et al. "Multiple Antigen Immunization of Infants Against Poliomyelitis, Diphtheria, Pertussis, and Tetanus", *Pediatrics*, pp. 720–736 (Nov. 1962).

Blom, et al. "The Swedish childhood diabetes study: Vaccinations and Infections as risk determinants for diabetes in childhood", *Diabetologia*, 34:176–181 (1991).

Classen, et al., Evidence That Cyclosporine Treatment During Pregnancy Predisposes Offspring to Develop Autoantibodies, Transplantation, Vol 51, No. 5, pp. 1052–1057, May 1991.

Dengrove et al. IgG and IgG Subclass Specific Antibody Responses to Diphtheria and Tetanus Toxoids in Newborns and Infants Given DTP Immunization, Pediatric Research, Vol. 20 No. 8, pp. 735–739, 1986.

Elias et al, Vaccination against autoimmune mouse diabetes with a T–cell epitope of the human 65–kDa heat shock protein, Natl. Acad. Sci. USA, Vol. 88, pp. 3088–3091, Apr. 1991.

Elias et al, Induction and therapy of autoimmune diabetes in the non–obese diabetic (NOD/Lt) mouse by a 65–kDa heat shock protein, Proc. Natl. Acad. Sci. USA, Vol. 87, pp. 1576–1580, Feb. 1990.

Fagan McInerney, et al., Prevention of Insulitis and Diabetes Onset by Treatment With Complete Freund's Adjuvant in NOD Mice, Diabetes, Vol. 40, pp. 715–725, Jun. 1991.

General Recommendations on Immunization, JAMA, Vol. 262 No. 1, pp. 22–26, Jul. 7, 1989 (from the CDC).

General Recommendations on Immunization, JAMA, Vol. 262, No 3, pp. 339–340, Jul. 21, 1989 (from the CDC).

Grange et al. BCG vaccination and cancer, Tubercle, Vol. 71, pp. 61–64.

Green et al. Incidence of childhood–onset insulin dependent diabetes mellitus: the Eurodiab Ace study, The Lancet, Vol. 339, pp. 905–909, Apr. 11, 1992.

Halsey et al. The efficacy of DPT and oral poliomyelitis immunization schedules initiated from birth to 12 weeks of age, Bulletin of the World Health Organization, Vol. 63 (6), pp. 1151–1169, 1985.

Harada, et al., Prevention of overt diabetes and insulitis in NOD mice by a single BCG vaccination, Diabetes Research and Clinical Practice, Vol. 8, pp. 85–89, 1990.

Huang et al. Pertussigen Treatment Retards, But Fails To Prevent, The Development of Type I, Insulin–Dependent Diabetes Mellitus (IDDM) In NOD Mice, Autoimmunity, Vol. 9, pp. 311–317, 1991.

Huang et al, The Effect of Pertussis Vaccine on the Insulin–Dependent Diabetes induced by Streptozocin in Mice, Pediatric Research, Vol. 18, No. 2, pp. 221–226, 1984.

Imamura et al. Intrapericardial OK–432 Installation for the Management of Malignant Pericardial Effusion, Cancer, Vol. 68 No. 3, pp. 259–263, Jul. 15, 1991.

John, T. Jacob, Immune response of neonates to oral poliomyelitis vaccine, British Medical Journal, Vol. 289, pp. 881, Oct. 6, 1984.

(List continued on next page.)

*Primary Examiner*—George C. Elliott
*Assistant Examiner*—Johnny F. Railey, II
*Attorney, Agent, or Firm*—Iver P. Cooper

[57] ABSTRACT

A method of immunization, and compositions therefor, are provided for substantially preventing or reducing the symptoms of at least one infectious disease and at least one chronic immune mediated disorder. An immunogenic challenge which supplements the normal childhood immunization schedule can help ensure the proper maturation of the immune system and prevent the development of chronic immune mediated disorders.

42 Claims, 2 Drawing Sheets

OTHER PUBLICATIONS

Kolb et al, Analysis of 22 Immunomodulatory Substances for Efficacy in Low-Dose Streptozotocin-Induced Diabetes, Diabetes Research, Vol. 6, pp. 21-27, 1987.

Krolewski et al, Epidemiologic Approach to The Etiology of Type I Diabetes Mellitus and its Complications, The New England Journal of Medicine, Vol. 317 No. 22, pp. 1390-1398, Nov. 26, 1987.

Madore et al, Safety and Immunologic Response to Haemophilus Influenzae Type b Oligosaccharide-CRM Conjugate Vaccine in 1- to 6-Month-Old Infants, Pediatrics, Vol. 85 No. 3, pp. 331-337, Mar. 1990.

Mukai et al, Combination Therapy of Local Administration of OK-432 and Radiation for Esophageal Cancer, Int. J. Radiation Oncology Biol. Phys., Vol. 22 No. 5, pp. 1047-1050, 1992.

Ogita et al, OK-432 Therapy for Unresectable Lymphangiomas in Children, Journal of Pediatric Surgery, Vol. 26 No. 3, pp. 263-270, Mar. 1991.

Oldstone, et al., Viruses as Therapeutic Agents, J. Exp. Med., Vol. 171, pp. 2091-2100, Jun. 1990.

Oldstone, Michael B.A., Prevention of Type I Diabetes in Nonobese Diabetic Mice by Virus Infection, Science, Vol. 239, pp. 500-502, Jan. 29, 1988.

Pabst et al, Effect of breast-feeding on antibody response to conjugate vaccine, The Lancet, Vol. 336, pp. 269-270, Aug. 4, 1990.

Pearce et al, Studies of Concanavalin A in Nonobese Diabetic Mice. I. Prevention of Insulin-Dependent Diabetes, The Journal of Pharmacology Experimental Therapeutics, Vol. 258 No. 2, pp. 710-715, 1991.

Perkins et al, Serological Response of Infants To Poliomyelitis Vaccine, British Medical Journal, pp. 68-71, Jul. 12, 1958.

Provenzano et al, Immunization and Antibody Response in the Newborn Infant, The New England Journal of Medicine, Vol. 273, No. 18, pp. 959-965, Oct. 28, 1965.

Sadelain, et al., Prevention of Type I Diabetes in NOD Mice by Adjuvant Immunotherapy, Diabetes, Vol. 39, pp. 583-589, May 1990.

Satoh et al, Treatment With Streptococcal Preparation (OK-432) Suppresses Anti-Inlet Autoimmunity and Prevents Diabetes in BB Rats, Diabetes, Vol. 37, pp. 1188-1194, Sep. 1988.

Satoh et al, Recombinant Human Tumor Necrosis Factor∝ Suppresses Autoimmune Diabetes in Nonobese Diabetic Mice, Rapid Publication, Vol. 84, pp. 1345-1348, Oct. 1989.

Schwimmbeck, et al., Abrogation of Diabetes in BB Rats by Acute Virus Infection, Association of Viral-Lymphocyte Interactions, The Journal of Immunology, Vol. 140, No. 10, pp. 3394-3400, May 15, 1988.

Seino et al, Inhibition of autoimmune diabetes in NOD mice with serum form streptococcal preparation (OK-432)-injected mice, Clin. exp. Immunol., Vol. 86, pp. 413-418, 1991.

Shintani, et al., Mechanism of Action of A Streptococcal Preparation (OK-432) in Prevention of Autoimmune Diabetes in NOD Mice, The Journal of Immunology, Vol. 144, No. 1, pp. 136-141, Jan. 1, 1990.

Simultaneous Administration of Multiple Vaccines, Active Immunization, pp. 16-19.

Spigland et al, Immunization of Infants With Formalinized Poliomyelitis Vaccine (Salk Type), Pediatrics, Vol. 25, pp. 812-821, May 1960.

Toyota et al, Islet Activating Protein (IAP) Derived from the Culture Supernatant Fluid of Bordetella Pertussis: Effect on Spontaneous Diabetic Rats, Diabetologia, Vol. 14, pp. 319-323.

Toyota et al, Streptococcal Preparation (OK-432) Inhibits Development of Type I Diabetes in NOD Mice, Diabetes, Vol. 35, pp. 496-499, April 1986.

Vagede et al., Vaccine Technology, Vol. 23, pp. 628-643.

Wheeley et al, Hepatitis B Vaccine in the Prevention of Perinatally Transmitted Hepatitis B Virus infection: Final Report on a West Midlands Pilot Study, Journal of Medical Virology, Vol. 30, pp. 113-116, 1990.

Herold, Kevan C et at, Prevention of Autoimm. Diab. 2/Nonactivity Anti-CD3 Monoctonal Antibody , Diabetes, Vol. 41, pp. 385-391 infectious Disease Ch. 3 Prevention of Infection pp. 21-24 "Immunization Procedures for Adults", Mar. 1992.

Mihara, Masahiko et at, Autoimmune Kidney Disease in MRL/lPr Mice Inhibited by OK-132; II. Effect of Indomethacin, J. Pharmacobio-Dyn., 15: 255-259, 1992.

Mihara, M. et al., Autoimmune Kidney Disease in MRL/Mp-Ipr mice inhibited by OK-432, a streptococcal preparation, Clin. exp. Immunol. 78:102-107, 1989.

Guberski, D.L. et at., Induction of Type I Diabetes by Kilham's Rat Virus in Diabetes-Resistant BB/Wor Rats, Science, 25:1010-1013, 15 Nov. 1991.

Luh, Kwen-Tay, et al., Comparison of OK-432 and Mitomycin C Pleurodesis for Malignant Pleural Effusion Caused by Lung Cancer, Cancer, 69:674-679, Feb. 1, 1992.

Hems, Gordon et al., B.C.G. and Leukemia, The Lancet, p. 183, Jan. 23, 1971.

Salonen, Tuula et al., Risk Indicators in Childhood Malignancies, Int. J. Cancer, 15:941-946, 1975.

Infectious Disease, Chapter 3, Prevention of Infection, Immunization Procedures for Adults, pp. 21-24.

Shinoda, M. et al., Treatment of advanced renal cell carcinoma with interferon alpha and OK-432 (streptococcal preparation), Acta Urologica Japonica, 38:1299-304, Nov. 1992.

Ferreri et al., Curr. Ther. Res. 52(3):493-497 (1992), (abstract only).

Ferreri et al., G. Mal. Infett. Parassit. 43(2):150-151 (1991), (abstract only).

METHOD AND COMPOSITION FOR AN EARLY VACCINE TO PROTECT AGAINST BOTH COMMON INFECTIOUS DISEASES AND CHRONIC IMMUNE MEDIATED DISORDERS OR THEIR SEQUELAE

BACKGROUND OF THE INVENTION

1. Field of the Invention

The present invention involves the fields of immunology and medicine, and more particularly relates to pediatric and/or supplemental immunization and compositions used therewith for immunizing mammals, such as humans, against both at least one infectious disease and at least one chronic immune mediated disorder.

2. Related Background Art

Pediatric Immunization

A number of severe childhood diseases can strike early in life. Pertussis may pose a serious threat to infants under three months of age, and, during the heyday of the polio epidemic, paralytic cases were reported in the 6–12 month age group with disturbing frequency.

Consequently, to avoid any gap in immunity, it was thought desirable to initiate immunization before infants lost passive protection from maternal antibodies. However, the presence of maternal antibodies can modify or suppress the infant's response to immunization, especially if the vaccine preparations are of low potency. The maturity of the infant's immune system is also a consideration, and premature immunization can result in immunological paralysis.

Accordingly, it has been generally recommended to postpone immunizations in developed countries where maternal antibodies provide protection against infant infectious diseases until after the age of 2 to 6 months, when the modifying effect of the maternal antibodies had disappeared. Therefore, immunizations should induce an active immune response before the infant loses this passive protection, so that there will be continuous protection from birth without any gap in immunity to natural diseases.

More recently, it has generally been recommended to begin infant immunizations, such as DTP (diphtheria, tetanus and pertussis) and OPV (oral polio virus), at younger ages, and many countries have carried out successful immunization studies and programs beginning at 6–8 weeks of age in developed countries (Expanded Programme on immunization (1984); (1985)). Accordingly, current recommendations for infant immunization is to provide routine DTP and OPV immunization initiated at no earlier than 6 weeks of age in all developed countries.

The literature on immunization schedules for pediatric vaccines is voluminous, but the examples which follow indicate what has been tried.

Provenzano et al., New England J. Med., 273:959–965 (1965) gave a first dose of a plain pertussis vaccine at 6–24 hours after birth. In Group I, two more such doses were given at three week intervals, and then two doses of combined diphtheria, tetanus and pertussis vaccine (DTP) at one month intervals. In Group II, the initial plain pertussis immunization was followed by three DTP injections at one month intervals.

The authors reported that the immunization response in both groups was inadequate, and attributed it to immunological paralysis "induced by the vigorous immunization schedule employed and the initiation of immunization on the first day of life." In view of earlier studies, they recommended that immunization not be attempted under three weeks of age.

Dengrave, et al., Pediatric Res., 20:735 (1986) gave a first dose of DTP to infants before 4 days of age, and further doses at 2, 4 and 6 months of age. The immune responses to diphtheria and tetanus immunogens were acceptable, in contrast to their previous demonstration that "an early neonatal dose of DTP resulted in a lowered pertussis antibody response in the subgroup of infants who had low maternally acquired levels of antibody."

The immunization protocol used by Baraff, et al., Pediatrics, 73:38–42 (1984) was similar, but the technology used to evaluate the immune response was more sophisticated. It was found that the IgG response to the pertussis lymphocytosis-promoting toxin (LPT) was lower and the IgM anti-FHA (filamentous hemagglutinin) response higher in the early immunization group than in controls. The authors were of the opinion that the anti-LPT response was of greater clinical significance and therefore concluded that neonatal immunization may be disadvantageous.

Perkins, et al., British Medical J., 68–71 (Jul. 12, 1958) investigated the response of infants to immunization with a killed poliomyelitis vaccine. The first dose was given to Group A at 1 week of age, Group B at 6 weeks of age, and Group C at 10 weeks of age. A second dose was given four weeks later. Three different virus types were tested in these three groups.

Perkins et al. found that maternally transmitted antibodies interfered with the immune response of the infants to the vaccines. Maternal antibodies declined with age (the half life was about 21 days). The type 2 vaccine was the least susceptible to this interference, but according to table 4, it too, felt it (60% of Group C infants responded, as compared to 35% of those in Group A).

Based on these findings, Perkins et al. concluded "in order to avoid the inhibiting effect of the placentally transmitted antibody, immunization should at present be delayed until six to nine months after birth."

Another study, by Spigland and Goldblum, Pediatrics 25:812–821 (1960) divided infants into groups A (1 and 2 months old), B (3 and 4 months old), and C (5 and 6 months old). Primary immunizations was either at (a) 0 and 21 days, or (b) 0, 7 and 21 days from the first immunization. The vaccine was the formalin-inactivated salk poliomyelitis vaccine. The authors concluded that "presence of maternal antibody seemed to interfere with active production of antibody," and that "the greater the age of primary immunization, the better the response."

In a recent pulse immunization study by John, British Medical Journal 289:88 (1984) the first dose of an oral poliomyelitis vaccine was given at 7, 14, 21, 28, 35 or 42 days of age, and the second and third doses at intervals of four weeks. The immune response to the oral vaccine, unlike the parenteral vaccine discussed previously, did not appear to be affected by the age of the infant. The authors recommended that children be immunized with the polio vaccine at 1 and 5 weeks, and with polio-plus-DPT at 9, 13, and 17 weeks. The present inventor believes that this immunization schedule would be disadvantageous as the late administration of pertussis would promote the development of diabetes and counteract any anti-diabetic effect of the early polio vaccine dosage.

Barrett, Jr., et al., J. Am. Med. Asso., 167:1103–6 (1958) considered whether it would be advantageous to combine the polio and DPT vaccines. The tetravalent vaccine was administered to children ranging in age from 2½ months to 5 years. Only polio antigen response was measured. The study found that "older children respond much more dramatically than do the infants."

Barrett, Jr. et al., Pediatrics, 30:720 (1962) gave a series of polio-DPT inoculations, beginning at various ages, and then at 1, 2, 3 and 4 months post-initial immunization. The first immunization was at (A) 1–2 days old, (B) 1–2 months old, (C) 3–4 months old or (D) 5–6 months old. Based on their observations, the authors recommended that the initiation of both polio and pertussis immunizations be withheld until the infants was three months of age.

A rather extensive review of the literature on DPT and oral poliomyelitis immunizations has been given by Halsey and Galazky Bull. World Health org., 63:1151–69 (1985). They compare the antibody response following one dose of OPV at 1–12 weeks of life (Table 1) with that to 2–3 doses beginning at 6–8 weeks of life (Table 2), and recommend that in countries where polio-myelitis has not been controlled, trivalent OPV be given at birth and at 6, 10 and 14 weeks of age. Pertussis vaccine schedules are reviewed in Table 3. The response to immunization beginning at 4 or more weeks was said to be almost as good as the results obtained by beginning at 8 or more weeks. They recommended initiating DPT at 6 weeks of age.

Infants as young as one month at the time of initial immunization have received a *Hemophilus influenzae* (bacterial meningitis) vaccine (three doses at two month intervals.) Madore, et al., Pediatrics, 85:331–337 (1990). Neonatal vaccination with Bacille Calmette-Guerin (BCG), and its impact on malignant disease, is briefly addressed by Grange and Stanford, Tubercle 71:61–64 (1990). A four dose vaccination schedule has been used to interrupt perinatal vertical transmission of hepatitis B virus, the first being given in the first week of life, and others at 1, 3 and 6 months of age.

Chronic Immune Mediated Disorders

Many chronic immune mediated disorders, such as immune mediated cancers and hyperactive immune responses, can be induced or inhibited by cells of the immune system. Environmental stimuli can affect whether those genetically predisposed to a chronic immune mediated disorder will develop symptoms or not. For example, it is not uncommon for one identical twin to have a chronic immune mediated disorder (e.g., type I diabetes mellitus) and the other identical twin to be free of the disorder. Several methods have been used to modulate an immune response in order to treat autoimmunity or early stages of diabetes mellitus (e.g., as disclosed in U.S. Pat. No. 4,710,380). These methods may include immunosuppressive agents. Immunosuppressive agents including general immunosuppressants and antigen specific tolerizing agents have been used to some extent to inhibit or treat chronic immune mediated disorders like autoimmunity. General immunosuppressants can lead to overwhelming infections and other toxicities as in bone destruction associated with corticosteroids and kidney disease associated with cyclosporine.

Effects of Tolerogens on Immune Disorders

Antigen—specific agents that cross-react to a specific autoantigen have been employed to down-regulate immune responses to a particular autoantigen. An example of this approach is contained in PCT patent application (PCT/US90/01397, WO/10449) which discloses the use of antigens which cross-react with a 65 Kd heat shock protein as tolerizing agents. Alternatively, PCT/US91/00240 (WO 92/00755) discloses utilizing sub-immunogenic amounts of an antigen which cross-reacts to alloimmune serum, in order to tolerize individuals. The problem with antigen specific agents is that one often does not know all the autoantigens involved in an autoimmune disease and the mechanism requires knowledge of such molecules.

Effect of Immunogens on Immune Disorders

Harada, et al. (1990) reported that a single intravenous injection of live BCG into 5 or 10 week old NOD mice suppressed insulitis and overt diabetes, while an injection into 15 week old mice was somewhat less suppressive.

The dose given by Harada, 0.25–1 mg, is, on a per kg body weight basis, equivalent to a human dose which would not be pharmaceutically acceptable. The animals were not vaccinated against any disease organisms other than BCG, and therefore were not necessarily representative of human infants, who are required by law (in the U.S.A.) to receive certain vaccinations. The immunization was with a live organism, and it is unclear whether Harada's findings may be extrapolated to immunization with inactivated organisms or with purified antigens. BCG vaccination has also been inconclusively reported to be associated epidemiologically with both an increased (Salonen, 1975) and decreased (Hems, 1971) incidence of childhood leukemia (Grange, 1990).

Huang, et al (1984) administered one dose of a whole cell *Bordetella pertussis* vaccine to mice which were at least 45 days old. The dose was given from 10 days before to 30 days after injection of streptozotocin (STZ), which produces a form of insulin-dependent diabetes. The pertussis vaccine aborted the development of IDD as a result of a single injection of STZ. Kolb, et al (1987) also looked at the effects of a pertussis vaccine in a streptozotocin-induced diabetes mouse model. The streptozotocin was administered when the mice were 8–11 weeks of age. The vaccine was given at day −3, +8, or +14 relative to STZ initiation. Given at day −3, it partially suppressed the hyperglycemia, while when given at days −8 and −14, it strongly enhanced it.

As admitted by Huang et al. (1991), "results from streptozotocin-induced IDDM experiments are difficult to extrapolate to type I IDDM because the correlation between chemically-induced diabetes and a "natural" development of autoimmune diabetes is unclear." Consequently, Huang et al (1991) examined the anti-diabetic effect of pertussigen in the genetically predisposed NOD mouse. These mice were give four injections of pertussigen at four week intervals, starting when the mice were 2 (Group 1) or 4 (Group 2 and 3) weeks of age. According to the authors, "although the time at which IDDM was first observed was delayed by several weeks, the incidence rates were not significantly different from those of untreated control NOD mice."

Toyota et al (1978) administered the islet activating protein of *Bordetella pertussis* to spontaneously diabetic rats having a weight of 300–400 g. While the age of the rats is not stated, this body weight could not be attributed to a rat younger than 42 days. Further more, the animals were already diabetic before the administration of the protein thus the administration was intended as a therapy as opposed to a method of immunization Effects of Immunomodulators on Immune Disorders Several papers discuss the effect of OK-432, a streptococcal preparation, on diabetes in mice. (Toyota, et al. 1986; Shintani, et al. 1990). Toyota et al., 1986, gave two clinical units of OK-432 to mice every week from 4–24 weeks of age. Shintani, et al. (1990) also tested schedules of weekly immunization at 4–15, 4–9, and 10–15 weeks of age. Weekly injections were needed at a dose of approximately 0.1 mg/20 g, (5 mg/kg or 100 KE/kg) mouse to provide the protective effect (Shintani, Satoh, Seino, et al 1990), while pharmaceutically acceptable clinical doses would be 0.07 KE/kg or 1400 times less.

OK-432 is a pyretic agent. See Shinoda, et al. Acta Urologica Japonica, 38:1299–13 ct (1992); Luh et al., Cancer, 69:674-9 (1992), Imamura, et al., Cancer, 68:259-63 (1991); Ogita, et al., J. Pediatric Surgery, 26:263-8 (1991). While it may be reasonable to prescribe it to a patient with cancer, it would not be clinically indicated for prevention of diabetes in youngsters. Young children are particularly prone to seizures as a result of high fevers. Ogita et al. used OK-432 only to treat surgically unresectable lymphangiomas in children.

It has also been found that lymphocytic choriomeningitis virus can prevent the development of diabetes in mice inoculated with LCMV shortly after birth (Oldstone, 1990), or at 30 days (Schwimmbeck) or 6 weeks (Oldstone, 1988) of age. It is not known whether this result occurs through induction of immunity. In any event, lymphotropic viruses are potentially very dangerous, as the case of HIV illustrates, and it would be difficult to win clinical acceptance of such a virus as a human therapeutic agent. Moreover the administration of other viruses has been shown to increase the incidence of diabetes (Guberski et al, 1991).

Several other agents have to be used in attempts to alter the development of immune mediated disorders. Specific lymphokines like IL-2 (e.g., according to Serreze et al, 1989) and tumor necrosis factor (e.g., according to Satoh et al, 1989) have also been employed to attempt to treat or prevent immune mediated disorders thought to be caused by lymphokine defects, by using multiple injections. However, purified lymphokines are relatively toxic, and expensive, and have short half lives.

Freund's adjuvant (Sadelain et al, 1990) has also been used to delay the development of diabetes in NOD mice. However, this adjuvant is not suitable for vaccine use in mammals at levels comparable to those used by Sadelein et al, (1990) due to its toxic effects. Freund's adjuvant can cause plasmacytomas as well as granulomas.

The use of anti-receptor and immune modulating agents (such as products that can block specific receptors, activate specific receptors, or cause the release of suppressor factors) generally requires repeated injections at high doses, e.g., in the mg/kg of body weight range. Examples of anti-receptor immunogens include monoclonal antibodies (e.g., U.S. Pat. No. 4,695,459) and lectins like Concanavalin A (e.g., Pearce and Peterson, 1991). Pharmaceutical use of monoclonal antibodies reactive to the antigen specific T-cell receptor have been shown to be associated with an increase in human lymphoid tumors and thus anti-receptor ligands reactive to the this T-cell receptor are unlikely to be pharmaceutically acceptable.

Accordingly, it has heretofore not been clearly shown that pharmaceutically acceptable doses of pharmaceutically acceptable immunogenic agents can prevent chronic immune mediated disorders. The related art has also not demonstrated whether such agents would be of value in preventing chronic immune mediated disorders in mammals as in humans that already receive immunogens early in life. The related art has also not shown when or how to administer such agents to a mammal which is already receiving immunogens early in life, in order to prevent or reduce the prevalence/incidence/frequency/severity of chronic immune mediated disorders.

Citation of documents herein is not intended as an admission that any of the documents cited herein is pertinent prior art, or an admission that the cited documents is considered material to the patentability of any of the claims of the present application. All statements as to the date or representation as to the contents of these documents is based on the information available to the applicant and does not constitute any admission as to the correctness of the dates or contents of these documents.

SUMMARY OF THE INVENTION

The present invention may be used to overcome one or more deficiencies of the related art.

It relates to the discovery that a supplemental childhood immunization schedule of immunization with a pediatric or non-pediatric immunogen, starting prior to 42 days of age, can facilitate maturation and/or development of the immune system, and/or substantially decrease the incidence, frequency, prevalence or severity of, or prevent, at least one chronic immune mediated disorder, and/or a surrogate marker thereof, in addition to protection against at least one infectious diseases, depending on the immunogenic agent or immunogen used.

Without intending to be bound by any theory, early administration of immunogens can cause the release of lymphokines that may accelerate the maturation of the immune system. The immunization may act in several ways including:

A. Enhancing destruction of autoimmune prone cells in the thymus;

B. Enhancing the flow of normal T-cells from the thymus;

C. Causing peripheral elimination of autoreactive T-cells that have escaped the thymus;

D. Causing the release of interferons which prevent infection with autoimmune causing viruses; and/or E. Causing migration of macrophages into the area of administration as in an injection site and away from an vital organ like the islet cells of the pancreas. The invading macrophages have the ability to act as antigen presenting cells and induce an autoimmune response against the vital tissue.

In contrast, the late administration of an immunogen can cause the release of lymphokines which may act as growth factors enabling autoimmune inducing cells to grown.

In preferred embodiments, the immunization schedules of the present invention may include employing initiating immunization prior to 28 days, supraimmunogenic doses, multiple doses prior to 56 or 112 days of age and/or dosing intervals of less than 28 days.

At least one non-pediatric immunogen(e.g. anthrax or plague immunogens) may be administered according to the present invention using similar immunization and dosing schedules to further strengthen the effect caused by administration of at least one pediatric immunogen described herein.

New pharmaceutical agents of the present invention are described that contain both non-pediatric and pediatric immunogens. Methods of manufacturing such agents are also included. Kits are described containing as receptacles at least one non-pediatric immunogen and at least one pediatric immunogen.

Methods are also provided for screening immunogenic agents for their ability to modulate the development of at least one chronic immune mediated disorder in a mammal such as a human.

The present invention is especially useful in preventing diabetes mellitus.

Other objects, features and advantages of the present invention will be clear to those skilled in one or more of the relevant arts, based on the teachings and guidance presented herein.

DETAILED DESCRIPTION OF THE PREFERRED EMBODIMENTS OF THE INVENTION

I. Introduction

Figure 1:
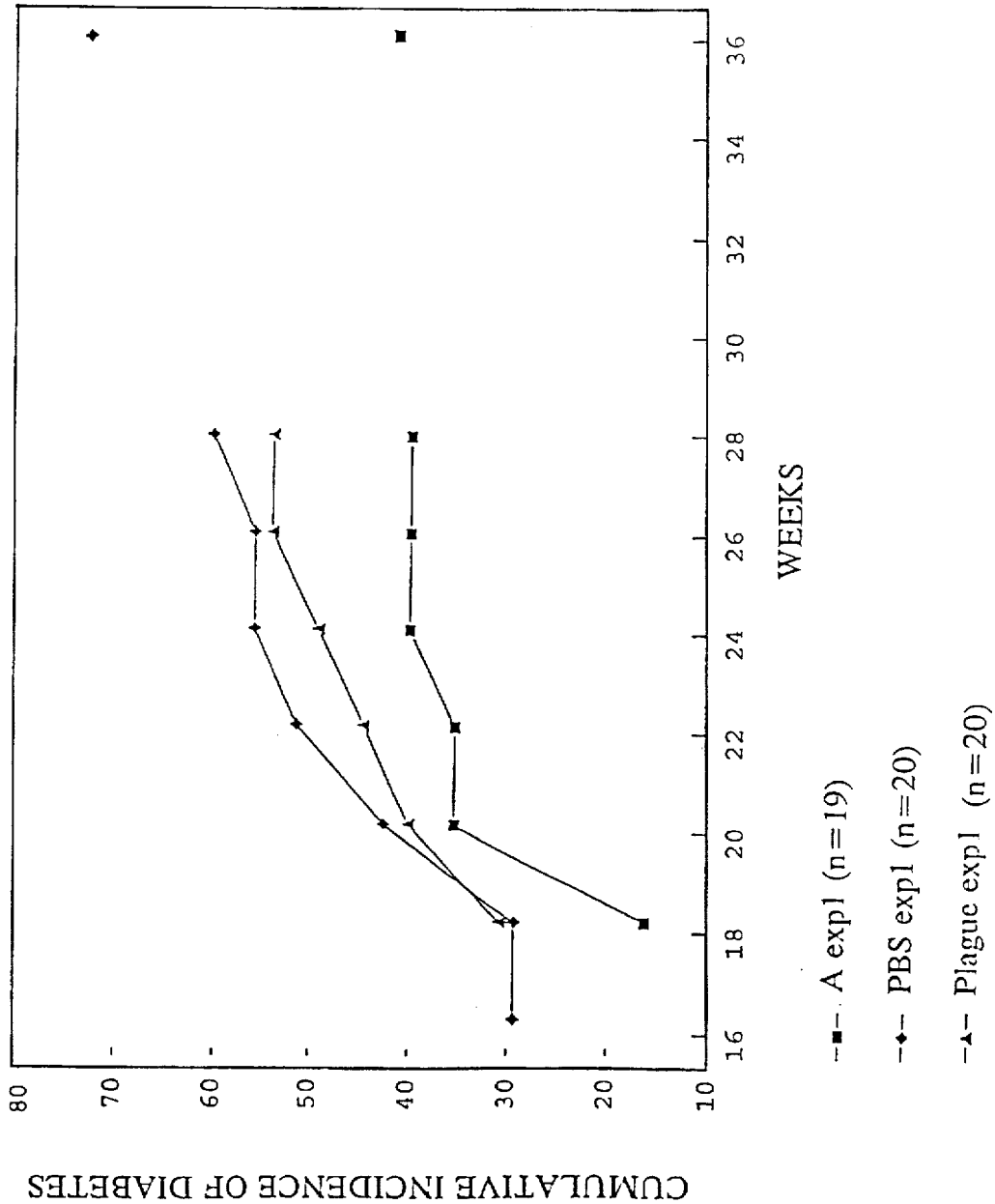
FIG. 1 depicts data from Example 1. Results show that mice receiving anthrax vaccine (A exp1) reached a peak cumulative incidence of diabetes of 42.1% at 24 weeks of life and no new cases of diabetes were detected through week 36 of life. The control receiving PBS (PBS exp1) showed a steady increase in the cumulative incidence of diabetes and 75% of mice had become diabetic by 36 weeks of life. Those animals receiving the plague vaccine (Plague exp1) had a lower incidence of diabetes than the controls throughout most of their life span. The plague vaccine treated animals had a cumulative incidence of diabetes of 57.9% at 28 weeks and development of diabetes appeared to be leveling off after 26 weeks. Plague vaccine treated animals were sacrificed at 28 weeks.

The present invention relates to methods and compositions involving administration and/or supplemental administration of sufficient amounts of pharmaceutically acceptable immunogenic agents to reduce the incidence, prevalence, frequency and/or severity of at least one chronic immune mediated disorder, and/or at least one surrogate marker of said disorder and to prevent at least one infectious disease. The invention further provides compositions and methods to prevent or to reduce the incidence, prevalence, frequency or severity of at least one chronic immune mediated disorder in a mammal, such as a human, which mammal receives an extensive immunization protocol early in life to prevent certain infectious diseases.

It has not been clearly shown before that pharmaceutically acceptable amounts of pharmaceutically acceptable immunogenic agents can be used to immunize against at least one chronic immune mediated disorder. The related art had further not demonstrated whether such agents would be of value in preventing chronic immune mediated disorders in mammals (e.g., in humans) that already receive immunogens early in life, in order to immunize against both at least one (and preferably, more than one) infectious disease and at least one chronic immune mediated disorder. The related art has not shown when or how to administer such agents to a mammal which is already receiving immunogens early in life. The related art has also not conclusively demonstrated that pharmaceutically acceptable amounts of pharmaceutically acceptable vaccines can induce diabetes mellitus and chronic immune mediated disorders or increase the risk of said diseases in a group receiving said vaccine. This failure is in part do to a long held belief that diabetes and other chronic immune mediated disorders develop because of an environmental insult that occurs in a time span of a few years before symptoms appear.

The lack of concern over the ability of vaccines to induce a chronic immune mediated disorder (e.g., but not limited to, diabetes) is evidenced by the lack of warnings on package inserts and labels of such products about such diseases. The related art had recommended administration schedules that induce high levels of antibodies protective against the targeted infectious agent. These dosing schedules included starting the administration of DTP at 6 weeks to 2 months. This dosing schedule is here determined to be capable of causing and/or substantially contributing to the development of chronic immune mediated disorders, e.g., as discussed herein.

The related art had administered vaccines interchangeably based on their ability to induce protective antibodies as well as a lack of evidence of acute toxicity (MMWR 1992, Merck Sharp Dome 1991). For example, a patient may receive a DTP vaccine from one manufacturer and a month later receive a second vaccine from a different manufacturer. Prevailing wisdom had suggested that as long as protective antibodies were developed and patients did not develop acute allergic responses, then there was no reason to contradict the practice of interchanging vaccines. The present invention demonstrates, however, that immune responses can affect whether a person develops a chronic immune disorder or not. For example, primary challenges and secondary challenges with a given immunogen may induce different amounts of lymphokines.

Furthermore, the related art has not developed trials to scientifically demonstrate that vaccination can increase or decrease the risk of developing diabetes mellitus or chronic immune mediated disorders, nor have animal models been developed to detect such effects. Current trials with new vaccines only compare results to people who received standard immunization. If both groups received vaccination starting at 2 months, which is now discovered to be associated with the increased risk then both groups will be associated with a higher than necessary risk of diabetes and other chronic immune mediated disorders. Additionally, current vaccine trials are not designed to look for complications of diabetes or other chronic immune mediated disorders which may not occur until 15 years, or more, after a person is immunized. It has recently been suggested that vaccination against measles may influence a reduction in the incidence of diabetes, however the data obtained was inconclusive because it failed to look at those who did not receive the vaccine and who did not develop the disease (Blom, 1991). These individuals are now discovered to in fact be at lower risk for developing diabetes than those who received the vaccine.

The related art had shown that lymphokines can potentially exacerbate autoimmunity. It has been well accepted that vaccines causes the release of lymphokines by immune mediating cells. The present invention, however, gives evidence that such conventional administration of vaccines can induce diabetes, which is best explained by the release of lymphokines.

II. Immunogenics Agents

Suitable immunogenic agents of the present invention preferably include at least one of any immunogen that is capable, of inducing a sustained, systemic, immune response at a suitable dose, without putting the infant at a substantially higher risk of developing an uncontrolled infection. Multiple immunogenic agents may be conditionally preferred to single agents, since a mammal's MHC type may be unresponsive to a particular antigen and multiple antigens may under appropriate conditions have the ability to activate more lymphocytic clones. Proteins as immunogenic agents may also be preferred to the extent that they are more effective in eliciting immune responses in newborns than carbohydrate or lipid immunogens.

Immunogens may also include certain classes of molecules that can cause the activation or reactivation of immune mediator cells, such as lymphocytes (B and/or T cells), macrophages and natural killer cells. Weak immunogens may be limited to the ability to invoke changes in such immune mediator cells, such as the release of lymphokines, altered cell movement, or altered composition of cell surface receptors. Strong immunogens have the additional ability to cause either an humoral immune response (such as, e.g., antibodies to said agent) or a cellular immune response (such as, e.g., a delayed type skin reaction to said agent). Non limiting examples of such immunogens include xenogeneic or allogenic proteins, while examples of non immunogens include molecules like water, oxygen, sodium chloride, and most syngeneic proteins.

Immunosuppressants like corticosteroids, azathioprine, cyclosporine, and FK-506 do not activate immune mediator cells and are not considered immunogens in this invention. Tolerogens also are not generally considered immunogens in this invention, except as a tolerogen-immunogen, as described herein. A tolerogen is generally defined as an agent which induces a state of antigen specific immunological unresponsiveness to an antigen that immunologically cross reacts to the agent. Tolerogens are further considered agents that inactivate immune mediator cells like B and T lymphocytes by reacting to their antigen specific binding sight and inactivating the cells in an antigen specific manor. However, if a tolerogen has a component that is clearly immunogenic and causes activation of immune mediator cells resulting in antibody formation or T cell immune responses, then it can be both a tolerogen and an immunogen. A tolerogen-immunogen in the latter case may be employed in this invention to prevent chronic immune disorders by down regulating cells that do not directly bind to the tolerogen and/or prevent chronic immune responses against organs/antigens that do not cross react immunologically to said tolerogen.

Immunogens or "conventional immunogens" correspond to a class of molecules that elicit an immune response through classical immunologic pathways as in the non-limiting example of the incorporation in an MHC molecule of antigen processing cell where the immunogens can potentially interact with antigen specific T cell receptors. Alternatively, as another non limiting example, conventional immunogens can bind to antigen specific binding regions of immunoglobulins which, (such as, e.g., if on the surface of B lymphocytes), may lead to modulating the B lymphocytes, but alternatively could cause modulation through other means, as in the activation of complement, or modulation of Fc receptors, as further non limiting subexamples.

There are several examples of conventional immunogens. The classical example is that of vaccines as in human vaccines. Such vaccines may be classified as living where such agents may multiply or perform homeostatic metabolic activity in the recipient, as in the live oral polio, live BCG, and live small pox vaccines, as non-limiting examples. Alternatively, conventional vaccines can be classified as inactivated (killed), where such agents have lost their ability to multiply or maintain homeostatic metabolic activity. Non-limiting examples of such killed vaccines include tetanus toxoid, diphtheria toxoid, and the killed whole cell pertussis vaccine. Other non-limiting examples of conventional non-living immunogens are haptens, anti-idiotype antibodies, and nucleic acid molecules, such as DNA or RNA, that can be expressed in cells as immunogenic molecules encoded by such nucleic acids. Alternatively, conventional immunogens may be classified according to their functional or structural properties in a microorganism such as capsular, fimbriae, nuclear, cell wall, membrane, and cytoplasmic immunogens.

immunogens are distinct from immune modulators There are several classes of immune modulators. One class is "immunocyte receptor ligands." Members of this class of agents bind to cell receptors of immune mediator cells in a non-antigen specific manner to cause the induction of an immune response, e.g., as defined herein. One subclass of this group is cytokines. Cytokines that are produced by lymphocytes are termed lymphokines, whereas peptides produced by monocytes or macrophages are given the term monokines. Thus, the terms cytokines, lymphokines, and interleukins may be used interchangeably to designate those peptide molecules that modulate host responses to foreign antigens or host injury by regulating the growth, mobility and differentiation of leukocytes and other cells.

Known cytokines include interleukins (IL) IL-1 (also endogenous pyrogen (EP), lymphocyte activating factor (LAF), mononuclear cell factor, catabolin, osteoclast activating factor and hematopoetin 1), IL-2 (also T cell growth factor (TCGF)), IL-3 (multicolony stimulating factor (M-CSF), P-cell stimulating factor, WEHI-3B factor, mast-cell growth factor and histamine-producing factor), IL-4 (B-cell growth factor (BCGF), B-cell stimulatory factor-1 (BSF-1), IL-5 (T-cell replacing factor (TRF), B-cell growth factor II (BCGF-II), eosinophil differentiation factor (EDF), IL-6 ($\beta_2$interferon (IFN-$\beta_2$), B-cell stimulating factor 2 (BSF-2), 26-kDa protein, hybridoma/plasmacytoma growth factor (HPGF or IL-HP-2), hepatocyte stimulating factor (HSF), and T-cell activating factor (TAF)), IL-7, IL-8 (neutrophil activating protein 1 (NAP-1), IL-10 (also cytokine synthesis inhibitory factor (CSIF); tissue necrosis factors (TNF) TNF$\alpha$ (also lymphotoxin (LT) and TNF$\beta$ (also macrophage derived TNF); interferons (IFN) IFN$\alpha$ and IFN$\beta$ (also type I IFN) and IFN$_\gamma$ (also type II IFN) and tissue growth factor (TGF) $\beta$.

Granulocyte-Macrophae Colony Stimulating Factor or GM-CSF is another non-limiting example of a cytokine in this class that causes the production of macrophages. Thymic hormones both natural and synthetic derivatives are another non-limiting example of receptor ligand and class of immune modulators, they are an example of a subclass of receptor ligands that cause division of immature immune mediator cells, in this case thymocytes or premature lymphocytes.

Cytokines modulate target cells by interacting with cytokine receptors on the target cell. Principal cell sources of cytokines include T lymphocytes, B lymphocytes, macrophages, stromal cells, monocytes, leukocytes, and platelets. While cytokine specific receptors are specific for a given cytokine, cytokine receptors are grouped into families based on shared features. The first group of cytokine receptors is the hemopoetin group which include immune system cells that bind IL-2, IL-3, IL-4, IL-6 and IL-7. A second receptor family is the TNF receptor family which bind both TNF$\alpha$ and TNF$\beta$. A third family is the immunoglobulin (Ig) superfamily receptor family, which contains an Ig sequence like motif and includes human IL-1 and IL-6 receptors.

See, e.g., Dawson, In *Lymphokines and Interleukins* (Dawson, ed.) CRC Press, Boca Raton, Fla. (1991); Mosmann et al, *Immunol. Rev.* 123:209–229 (1991); Mosmann et al, Immunol. Today 12:A59–A69 (1991); Sherry et al, *Curr.*

*Opinion Immunol.* 3:56–60 (1991); Paul, *Blood* 77:1859–1870 (1991); Dower et al, *J. Clin. Immunol.* 10:289–299 (1990).

A second subclass in this receptor ligand group include lectins. A non limiting example of a receptor ligand is a monoclonal antibody or fragment capable of binding and/or modulating a receptor, e.g., as a T cell receptor or an IL-2 receptor.

A second class of immune modulators are anti-receptor molecules. These agents can cause the production of antibodies or T cells that can either block receptors on a cell surface or kill such cells in a recipient. As non limiting examples, one skilled in the art could induce active immunization in a recipient leading to the formation of antibodies or cytotoxic T cells that could, e.g., block lymphokine receptors on a cell, neutralize certain subtypes of antibodies, kill B lymphocytes that make certain subtypes of antibodies, or kill T lymphocytes that have a certain subtype of receptors on their surface.

A third class of immune modulators are "transplanted cells," which may include immune mediator cells as defined above that can induce responses by releasing lymphokines or by secreting other molecules. As non-limiting examples these cells can be lymphocytes, macrophages, splenocytes and/or thymocytes. As non limiting examples the products the transplanted cells release can be lymphokines, as well as heterogenic or allogenic molecules as in proteins, carbohydrates and lipids.

A forth class of immune modulators are "general immune modulators." These agents also go by other names including immune modulating agents or immune response modulators. Depending on what dose and how these agents are given they can be termed immune potentiators or immunosuppressants. These agents often have the ability to cause non-antigen specific activation of immune mediator cells through the release of lymnphokines compared to vaccines that usually cause specific activation of clones with specific affinity for the vaccine antigens. General immune modulators are often used at higher doses than conventional immunogens and/or are typically given at frequent intervals as in every seven days or less. These agent often provide no protection against common pathogens in contrast to many vaccines and other pharmaceutically acceptable conventional immunogens. These agents generally do not employ adjuvants in contrast to vaccine immunogens. Non-limiting examples of immune modulators include the biologic OK-432 and the chemical entities levamisole and isoprinosine.

It should be noted that some agents may be members of more than one of the above groups or classes. As a non-limiting example, a lymphokine may be a conventional immunogen if it is derived from a heterologous species to which it is given as in the case of administering a mouse derived lymphokine to a human. Hybrid or fusion molecules can also be made that contain an biologically active part that has lymphokine activity and another section that contains an conventional immunogen.

Immunogenic agents of the present invention may include pediatric and non-pediatric immunogens. The term "pediatric immunogens" refers to immunogens that after birth were routinely administered to children prior to 112 days, in modern developed nations of moderate latitudes in 1992. These agents include but are not limited to BCG, measles, mumps, rubella, diphtheria, pertussis, hemophilus influenza, tetanus, hepatits B, and polio. Non-pediatric immunogens are immunogens not routinely administered to children prior to 112 days in modern developed nations of moderate latitude in 1992, and may include, but are not limited to, the group consisting of anthrax, yellow fever, plague, small pox, pneumococcus, cholera, varicella, adenovirus, meningitis, typhoid, herpes, hepatitis C, cytomegalovirus (CMV), HIV, influenza, malaria, rabies, and neisseria immunogens.

Immunogenic agents may also include, but are not limited to immunogens comprising at least one of any antigen derived from a virus, bacteria, yeast, mold, plant, insect, allogeneic or xenogeneic animal or a molecule, compound or composition that immunologically cross reacts with the antigen. Such agents may be made from the killed or live bacteria, killed or live viruses, recombinant or chemically synthesized or purified immunogenic agents including antigens, fragments or cross reacting synthetic or recombinantly produced peptides, carbohydrates, lipids or any combination thereof. Such agents can be combined with each other and with vaccines against infectious diseases to substantially prevent or reduce the incidence of immunologic disorders according to the present invention.

The terminology used regarding immunogen, as in the non limiting example of a polio immunogen, includes any molecules that are produced by an organism that causes polio as well as any molecules that cross reacts immunologically with the molecules. A polio immunogen therefore could include as non-limiting examples whole live viruses, killed viruses, a specific purified fraction derived from killed viruses, a specific molecule purified from killed viruses, a molecule made recombinantly, and a molecule made synthetically. The term "immunologically cross reacts" refers to molecules that induce antibodies or T-cells that bind to the cross reactive molecule or fragments thereof.

In a preferred embodiment, the immunogenic agent may comprise at least one anthrax vaccine immunogen and at least one pediatric and/or other non-pediatric immunogen. In another preferred embodiment, the immunogenic agent may contain at least one plague vaccine immunogen and at least one pediatric and/or other non-pediatric immunogen.

III. Pharmaceutical Preparations

This invention also includes immunogenic agents comprising immunogens that are in any pharmaceutically acceptable form. The term "pharmaceutically acceptable" has both a legal definition and a clinical definition. The code of federal regulations (21 CFR Part 600) legally defines what make an agent "pharmaceutically acceptable." Non-pharmaceutically acceptable products may be contaminated with agents, such as endotoxin or other pyrogens, the presence of which can have profound adverse effects on the immune system of the recipient. Results from immunologic experiments using an non-pharmaceutically acceptable agent e.g., a lymphokine contaminated by endotoxin, may be quite different from an identical experiment using said lymphokine produced under GMP which lacks said impurities.

Immunogenic agents may be prepared in pharmaceutically acceptable form according to known method steps, based on the teaching and guidance presented herein. Non-limiting examples of preparation of immunogenic agents suitable for use in the present invention include DTP (21 CFR, part 610–630; Mueller et al *J. Immunol.* 56:143 (1947)); tetanus/diphtheria Pillemer et al., *J. Immunol.* 54:213 (1946)); measles/mumps/rubella (U.S. Pat. No. 4,147,772 to McAleer et al); yellow fever (*Morbidity and Mortality Weekly Report* 27:268 (1978); HHS Publication No. (CDC) 81-8280, U.S. Gov't Printing Ofc., Washington, D.C. (1981)); typhoid (*Morbidity and Mortality Weekly Report* 27:231 (1978)); plague (*Morbidity and Mortality Weekly Report* 27:231 (1978)); Hepatitis B (U.S. Pat. No. 4,129,646, McAleer et al); hemophilus ((U.S. Pat. No. 4,196,192, Kuo); OPV (Eagle, *Science* 122:501 (1955); anthrax (FDA Freedom of Information Act document regarding Michigan Dept. of Health Anthrax Product License Application, 1993), the entire contents of which are herein entirely incorporated by reference.

Such immunogenic agents in pharmaceutically acceptable form may also be prepared according to known method steps using recombinant technology and by the use of monoclonal antibodies and fragments thereof. See, eog., Ausubel et al, eds, *Current Protocols in Molecular Biology*, Greene Publishing Assoc. and Wiley interscience, N.Y., N.Y. (1987, 1993); Coligan et al eds., Current Protocols in *Immunology*, Greene Publishing Assoc. and Wiley Interscience, N.Y., N.Y. (1992, 1993); Sanbrook et al infra, are Harlow, infra.

For the purpose of the present invention, an "immunogenic agent is" a pharmaceutical preparation which may comprise at least one immunogen, wherein the immunogen (s) are provided in the immunogenic agent in an amount effective to achieve its intended purpose. In addition to the immunogen, the pharmaceutical composition may contain suitable pharmaceutically acceptable carriers, such as excipients, carriers and/or auxiliaries which facilitate processing of the active compounds into preparations which can be used pharmaceutically. While each immunogen may be provided in subimmunogenic amounts, the total amount provided in a composition of the present invention is sufficient to provide an effective amount.

Such carriers are preferably adjuvants that release an immunogen in vivo over a prolonged period as compared to administration of an unbound immunogen. Non-limiting examples of such adjuvants are known vaccine adjuvants or depot adjuvants. Preferably the depot adjuvant comprises an aluminum, calcium or salts thereof, such as aluminum sulfate (alum), aluminum phosphate, calcium phosphate or aluminum hydroxide. See, e.g., Gregoriades, G. et al., *Immunological Adjuvants and Vaccines*, Plenum Press, New York, 1989; Michalek S.M. et al., Liposomes as Oral Adjuvants, *Curr. Top. Microbiol. Immunol.* 146:51–58 (1989), all incorporated by reference. Another non-limiting example of a preferred carrier is one that target macrophages and/or activates them, such as a liposome. Adjuvants that activate macrophages, may be added to carriers to increase their ability to activate macrophages.

Pharmaceutical compositions comprising at least one immunogen useful according to the present invention may also include suitable solutions for administration, intramuscularly, intravenously, subcutaneously, dermally, orally, mucosally, or rectally or by any other injection, and contain from about 0.001 to 99,999 percent, preferably from about 20 to 75 percent of active component (i.e. the immunogen) together with the excipient. Compositions which can be administered rectally include suppositories. Preparations of immunogenic agents for parenteral administration include sterile aqueous or non-aqueous solutions, suspensions, and emulsions, which may contain auxiliary agents or excipients, such as suitable adjuvants, which are known in the art. Pharmaceutical compositions such as tablets and capsules can also be prepared according to routine methods. See, e.g., Berker, supra, Goodman, supra, and Avery, supra, which are entirely incorporated herein by reference, included all references cited therein.

An immunogen that meets the legal definition of pharmaceutically acceptable must further meet the clinical definition of pharmaceutically acceptable. A clinical definition of pharmaceutically acceptable, as used herein, requires that said agent has a sufficiently beneficial clinical effect when used in a pharmaceutically acceptable dose.

A pharmaceutically acceptable dose, as in total dose, is a dose where the clinical benefits of said product outweighs the toxicity at said dose. Non limiting examples of said toxicity include acute or subacute reactions like fever, shock or seizures, which may lead to permanent sequela and chronic toxicity like cancer, as is known and recognized in the relevant arts. A pharmaceutically acceptable dose according to this definition can vary according to the severity of the illness being modulated by the immunogenic agent. It is logical that a high dose of an agent which causes significant toxicity may be pharmaceutically acceptable for treating a life threatening malignancy yet the same dose would not be pharmaceutically acceptable for treating a benign disorder like a common sore throat. Following said logic, vaccination or other regimens to prevent diseases in healthy individuals usually employ non toxic doses. In the case of vaccinations, permanent sequelae as infrequent as one in 300,000 following immunization, as is believed the case with the whole cell pertussis vaccine, may be considered unsuitable by some.

A pharmaceutically acceptable dose will depend on the structure of the particular agent and/or the condition or genotype of the recipient. Some agents may be more toxic than others while some may be more immunogenic than others. In a like manner some individuals are more responsive to a given dose while others may be more sensitive to the toxic effects at that dose. There is thus an individual variation within the definition of pharmaceutically acceptable dose as well as species, racial, age, and population variation, all of which should be taken into account when dosing an individual. Such consideration has, of course, been given to other prophylactic agents.

The term pharmaceutically acceptable dose as defined herein may also incorporate an economic definition. A pharmaceutical acceptable dose in terms of preventing disease is one where benefit to society approximates or is greater than the cost of administering the agent. Said cost of administering the agent may include the cost of the agent, the necessary supplies as in needles, any transportation needed to bring patient, and the staff expenses needed to administer said agent, maintaining an administration clinic, as well as the costs associated with or resulting from adverse reactions to the agent. The benefits to society include savings from reductions in costs associated with the diseases that are prevented in society include one or more of lost productivity, medical expenses, expenses related to the care of the disabled person and some or all complications stemming from the illness. As a non limiting example a pediatric vaccine that costs a society one trillion dollars a year to administer might not be considered pharmaceutically acceptable for a disease that costs said society 10 million dollars a year.

A pharmaceutically acceptable dose must usually be determined by performing screening tests for both efficacy and safety. Data presented herein shows that doses of vaccines approximating that used to protect humans against infectious diseases (immunogenic doses) were also effective in preventing chronic immune mediated disorders in certain mammals. Pharmaceutically acceptable immunogenic doses for many of the preferred agents presented herein are thus readily available through common references with an non-limiting example being the physician's desk reference, manufacturers product inserts, and scientific literature referenced through a database like MEDLINE. The immunogenic doses mentioned in the reference may be adjusted for the size of the recipient. A screening method as described herein may be used to calculate the optimal dose.

The term pharmaceutically acceptable dose includes a supraimmunogenic dose. The lowest dose of immunogen effective in protecting the recipient against an infectious disease is termed the immunogenic dose. Using higher doses than the immunogenic dose results in a higher morbidity and mortality caused by the immunization than the additional morbidity and mortality, related to the infectious disease, prevented by using the higher dose. The current invention teaches that doses above the immunogenic dose may lead to enhanced protection against chronic immune mediated disorders.

A supraimmunogenic dose may be defined in several ways. One definition may be a dose that is higher than has been used to induce an protective immune response against the intended pathogen in recipients of a given age/size. The immunogenic dose can be determined from art describing immunization against infectious diseases, as described herein. A second definition of supraimmunogenic dose may be a dose higher than necessary to prevent an infectious disease, where the enhanced toxicity associated with using the higher dose is greater than any measured benefit in preventing the intended infectious disease derived from using the higher dose. The toxicity and benefit may be determined by calculating the number of people expected to develop vaccine related toxicity and the number expected to be spared from the sequela of the infection disease that the vaccine prevents, where the toxicity and benefit may be quantitated into short term, moderate, and permanent sequelae. The toxicity and benefit may also be calculated financially as described herein.

The term pharmaceutically acceptable immunogen in this invention does not include the routine administration of common foods, such as bovine milk, common baby formula, and common baby food.

Preparations of immunogenic agents for parenteral administration include sterile aqueous or non-aqueous solutions, suspensions, and emulsions, which may contain auxiliary agents or excipients, such as suitable adjuvants, which are known in the art. Pharmaceutical compositions such as tablets and capsules can also be prepared according to routine methods.

IV. Pharmaceutical Administration

Another aspect of the present invention includes immunization of a mammal against at least one chronic immune mediated immune disorder by administration of at least one immunogenic agent of the present invention. Such a method for immunization of a mammal allows for both the prevention of certain infectious diseases as represented by relevant vaccines and chronic immune mediated diseases, and/or providing one or more of reduced incidence, prevalence, frequency and/or severity of at least one chronic immune related disorder, or a surrogate marker, thereof, and or at least one infectious or non-infectious disease.

Thus, it has now been discovered that the occurrence and/or severity of chronic immune mediated disorders, such as hyperactive immune responses and immune related cancers, may be substantially prevented, or their symptoms, prevalence, incidence, severity, or frequency reduced, by administration to a mammal, such as a human, at least one pharmaceutically acceptable dose of a pharmaceutically acceptable immunogenic agent, wherein the first pharmaceutically acceptable dose is given prior to the first 6–8 weeks of life. It was also unexpectedly found that immunization with conventional pediatric vaccines beginning at 6–8 weeks, which is the common immunization protocol in developed countries, actually can increase the probability that a mammal will develop a chronic immune mediated disorder.

Current vaccination protocols, such as childhood active immunization protocols (e.g., as presented in THE MERCK MANUAL, 16th ed., 60–64 and 1944–47 (1992) entirely incorporated herein by reference) may at best only slow the progression of immune mediated disorders, but not prevent them.

At least one pharmaceutically acceptable immunogenic agent, used in a method of the present invention may be administered by any means that achieve its intended purpose, for example, to substantially prevent or reduce the severity of a chronic immune mediated disorder, using an immunogenic agent in the form of a pharmaceutical composition.

For example, administration of such a composition may be by various parenteral routes such as subcutaneous, intravenous, intradermal, intramuscular, intraperitoneal, intranasal, transdermal, or buccal routes. Alternatively, or concurrently, administration may be by the oral route.

A preferred mode of using an immunogenic agent or composition of the present invention is by intramuscular application.

It is understood that the dosage of an immunogenic agent of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. In the context of the present invention "one dose" may include concurrent or separate administration of more than one immunogen comprised of an immunogenic agent according to the present invention. See, e.g., Berkow et al, eds., *The Merck Manual*, 16th edition. Merck and Co., Rahway, N.J., 1992; Goodman et al., eds., *Goodman and Gilman's The Pharmacological Basis of Therapeutics*, 8th edition. Pergamon Press, Inc., Elmsford, N.Y., (1990); *Avery's Drug Treatment: Principles and Practice of Clinical Pharmacology and Therapeutics*, 3rd edition. ADIS Press, LTD., Williams and Wilkins, Baltimore, Md. (1987), which references and references cited therein, are entirely incorporated herein by reference.

The total dose, as in an pharmaceutically acceptable dose, required for each treatment may be administered by multiple doses or in a single dose. An immunogenic agent may be administered alone or in conjunction with other therapeutics directed to immunologic disorders, such as allergies, immune mediated cancers and autoimmune pathologies, as known in the art.

Effective amounts of pharmaceutically acceptable dosages of at least one immunogenic agent or composition of the present invention, which may also include vaccines or carriers, are from a total amount of at least one immunogenic agent of about 0.01 µg to about 10 mg immunogen or active agent per kg body weight, and preferably from about 0.5 µg/kg to about 800 µg/kg body weight, such as 0.01–10.000 µg/kg, or any range or value therein. The active agent is the at least one immunogenic agent that induces an immune response according to the present invention. The safe dose will vary depending on the agent. Some immunogens are toxic at low doses while others are not.

V. Methods of Immunization Against at Least One Chronic Immune Mediated Disorder and Against at Least One Infectious Disease A chronic immune mediated disorder is one which lasts longer than two months, but does not include permanent sequela of acute immune response diseases such as seizures and anaphylaxis, nor do such disorders include diseases associated with live virus infections as in subacute sclerosing panencephalitis induced by measles vaccine. Chronic immune mediated disorders does not include sequela caused by chronic infections by live vaccines. The invention is especially useful in preventing chronic immune disorder which develop at least one year after a vaccination. Thus, an illness like Guillean-Barrea syndrome is not routinely considered an chronic immune mediated disorder.

A growing number of human diseases have been classified as autoimmune in nature (see, Theofiopoulos, A., In: D.P. Stites, et al., eds., *Basic and Clinical immunology*, Lange Medical Publications, Los Altos, Calif., 1988; and Berkow, supra), which references are entirely incorporated by reference, and the present invention is intended to include as a chronic immune mediated disorder any and all of such diseases, with the exception listed herein, in mammals including humans.

Methods and compositions of the present invention may be used for preventing and/or inhibiting chronic immune mediated disorders including immune mediated cancers and hyperactive immune responses. Such immune mediated cancers may include lymphoreticular neoplasia, lymphoblastic leukemia, brain tumors, gastric tumors, plasmacytomas, multiple myeloma, leukemia, connective tissue tumors, solid tumors and lymphomas. Such hyperactive immune responses may include asthma/allergies and autoimmune diseases. Such allergies may include hay fever, atopic dermatitis, urticaria, perennial rhinitis, allergic conjunctivitis, pulmonary diseases, food allergies, skin allergies, anaphylaxis (e.g., associated upon exposure to blood products) and pollinosis. Such autoimmune diseases may include conventional organ specific autoimmunity, neurological disease, rheumatic diseases/connective tissue disease, autoimmune cytopenias, and related autoimmune diseases. Such conventional organ specific autoimmunity may include thyroidiris (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scieroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjorgren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases, as presented herein and known in the related arts. See, e.g., Berkow et al., eds, supra, pages 303–364, 710–718, 1083, 1269, 1305–1377, 1338 1677–1684, and 2435–2438 which is entirely incorporated herein by reference.

Type I diabetes mellitus is defined herein as an naturally occurring or spontaneously developing disease of the pancreatic islet cells that is not intentionally induced. This definition is intended to differentiate the natural disease from altered insulin secretion following the deliberate or intentional destruction of pancreatic islet cells through the use of toxic agents, surgery or other bodily insults.

Type II diabetes mellitus will benefit from the invention as a non-limiting example. The etiology of this disorder is poorly understood. However, scientists believe some patients are unable to secrete enough insulin or are resistant to insulin. Scientists have not ruled out that many of these patients fail to produce enough insulin because they have insufficient islet cells. Scientific evidence suggests that failure to produce sufficient insulin in some type II diabetics is due to destruction of islet cells (Niskanen et al 1991). This evidence includes the presence of autoantibodies to islet cells. These patients differ from type I patients in that they produce enough insulin to prevent them from becoming ketotic and they develop disease later in life. A person who is resistant to insulin and needs more insulin to survive would be at a disadvantage if that person had lost a substantial amount of his or her islet cells do to an immune mediated attack earlier in life. A vaccine to protect islet cells would thus be advantages to people predisposed to type II diabetes. Accordingly, methods and immunogenic agents of the present invention provide a treatment for reducing the severity of incidence of diabetes.

There are multiple sequelae to chronic immune mediated disorders. As non-limiting examples, autoimmunity can result in end organ failure or cancer. Chronic inflammation, as occurs in chronic immune mediated disorders, can cause the release of molecules like serum amyloid which can cause pathology. Serum amyloid is associated with amyloidosis peripherally and senile dementia in the central nervous system. The present invention is intended to utilize low or non toxic agents that can be used to prevent disease in asymptomatic mammals without the need to screen them for risk of developing chronic immune mediated disorders, however the invention may be used in certain subpopulations at higher risk for developing the disorders than others. Alternatively the invention may be administered to a large number of mammals with different risks for developing a given chronic immune disorder and only certain subpopulations may be shown to benefit statistically from the administration. The subpopulations may include mammals at higher risk than the general population. Non-limiting examples of the subpopulations include those with family history of at least one chronic immune mediator disorder, those who are deemed at high risk because of genetic or biochemical screening of themselves or biological relatives, and those at risk because of an abnormal birth as in prematurity or small size.

A suitable regimen for preventing, suppressing, or treating an immunologic disorder, according to the present invention comprises administering an immune response effective amount of an immunogenic agent, to a mammal, wherein the immune response effective amount induces an immune response in the mammal, sufficient to reduce at least one measure selected from the group consisting of incidence, prevalence, frequency and severity of at least one chronic immune mediated disorder, and/or at least one surrogate marker of the disorder, in a population and/or subpopulation of the mammals.

Such a method may include immunization of a mammal less than 96 months of age against at least one and preferably more than one (e.g., at least three) infectious diseases and at least one chronic immune mediated disorder. The method may, in one aspect, comprise administering to a mammal at least a first dose of a pharmaceutically acceptable dose of at least one pharmaceutically acceptable immunogen wherein at least one immunogen, as in a single immunogen or combination of immunogens, is capable of inducing an immune response sufficient to reduce the severity of and/or prevent, at least three infectious diseases and reduce at least one measure in the group consisting of incidence, prevalence, frequency, and/or severity of at least one chronic immune mediated disorder and/or of at least one surrogate marker of the disorder in a population and/or subpopulation of mammals receiving the at least one pharmaceutically acceptable immunogen.

The at least three infectious diseases may include at least three members selected from the group consisting of diphtheria/tetanus/pertussis, polio, hepatitis B, hemophilus influenza, and measles/mumps/rubella. The at least one pharmaceutically acceptable immunogen may be selected from the group consisting of at least one diphtheria/tetanus/pertussis immunogen, polio immunogen, hepatitis B immunogen, hemophilus influenza immunogen, measles/mumps/rubella immunogen and non-pediatric immunogen.

The administration may be in one of the following three alternatives. In the first alterative method administration may include at least a first dose of at least three or more members selected from the group consisting of a diphtheria/tetanus/pertussis immunogen, polio immunogen, hepatitis B immunogen, hemophilus influenza immunogen, measles/mumps/rubella immunogen and a non-pediatric immunogen wherein the three members may each be administered under at least one condition, as in each may be administered at different times, selected from the group consisting of; (1) administering the first dose at less than 42 days of age of the mammal; (2) administering the first dose, the dose comprising at least a second dose, wherein the second dose and or any subsequent doses is administered less than 28 days after the preceding dose when the mammal is less than 175 days of age; and 3) administering at least one dose of the at least one pharmaceutically acceptable immunogen at a frequency selected from the group consisting of (A) at least four doses prior to the age of 112 days for the diphtheria/tetanus/pertussis immunogen, the hepatitis B immunogen and the hemophilus influenza immunogen; (B) at least five doses prior to the age of 112 days for the polio immunogen; and (C) at least 3 doses prior to the age of 147 days for the measles/mumps/rubella immunogen.

In a second alternative method administration may include at least one member selected from the group consisting of a diphtheria/tetanus/pertussis immunogen, polio immunogen, hepatitis B immunogen, hemophilus influenza immunogen, non-pediatric immunogen, and a measles/mumps/rubella immunogen wherein the at least one member is administered according to at least two conditions selected from the group consisting of; (1) administering the first dose at less than 42 days of age of the mammal; (2) administering the first dose, the dose comprising at least a second dose, wherein the second dose and or any subsequent doses is administered less than 28 days after the preceding dose when the mammal is less than 175 days of age; and (3) administering at least one dose of the at least one immunogenic agent at a frequency selected from the group consisting of (A) at least four doses prior to the age of 112 days for the diphtheria/tetanus/pertussis immunogen, the hepatitis B immunogen, the non-pediatric immunogen, and the hemophilus influenza immunogen; (B) at least five doses prior to the age of 112 days for the polio immunogen; and (C) at least 3 doses prior to the age of 147 days for the measles/mumps/rubella immunogen.

In the third alternative method administration may include at least one pharmaceutically acceptable immunogen which comprises at least one non-pediatric immunogen where administration of the non-pediatric immunogen may be at least one selected from the group consisting of (1) administering the first dose at less than 56 days of age of the mammal; (2) administering at least two doses, wherein the second dose and or any subsequent doses is administered less than 28 days after the preceding dose when the mammal is less than 175 days of age; and (3) administrating at least four doses prior to the age of 112 days for the non-pediatric immunogen.

The first dose may be administered at an age of at least 28 days, the doses may comprise a total of at least 4 separate doses prior to the age of 112 days, wherein each of the at least 4 separate doses may or may not contain the same or different immunogens and/or the same or different amounts of immunogens as the other separate doses.

The first dose may be administered at an age of less than 28 days, and the doses may comprise a total of at least 5 separate doses prior to the age of 112 days, wherein each of the at least 5 separate doses may or may not contain the same or different immunogens and/or the same or different amounts of immunogens as the other separate doses.

The interval between any two doses may be less than 28 days.

The administration may include 2 or all 3 alternative methods described above. The first alternative methods may include administering at least at least four members or all 5 members by at least one of the conditions described. The second alternative method may include administering one selected from the group consisting of at least 2, 3, 4, 5 members by at least two conditions. The at least two conditions may include at least 3 conditions. The third alternative method may include administering at least one non-pediatric immunogen by at least two condition or all three conditions.

The methods of the present invention may also provide a method for pediatric immunization against at least two infectious diseases, comprising administering at least one pharmaceutically acceptable dose of at least one pediatric vaccine to a mammal of at least 42 days of age, the improvement comprising further administering to the mammal at least one pharmaceutically acceptable dose of at least one pharmaceutically acceptable non-pediatric immunogen, wherein the administration is according to at least one step selected from the group consisting of; (1) administrating at least one dose of the non-pediatric immunogen at less than 56 days of age of the mammal; (2) administering two or more doses of the non-pediatric immunogen, at intervals less than 28 days when the mammal is less than 175 days of age; and (3) administrating at least four doses of the non-pediatric immunogen prior to the age of 112 days of the mammal; wherein the further administration reduces at least one measure selected from the group consisting of incidence, prevalence, frequency, and severity of at least one chronic immune mediated disorder and or of at least one surrogate marker of the disorder in a population and or subpopulation of the mammals.

The methods of the present invention also provide a method for pediatric immunization against at least two infectious diseases, comprising administering at least one pharmaceutically acceptable dose of diphtheria/tetanus/ pertussis vaccine to a mammal of at least 42 days of age, the improvement comprising further administering to the mammal at least one pharmaceutically acceptable dose of diphtheria/pertussis/tetanus vaccine, where the further administration is according to at least one method from the group consisting of; (1) administrating at least two doses of the diphtheria/tetanus/pertussis vaccine at less than 42 days of age of the mammal; (2) administering at least one dose of the diphtheria/tetanus/pertussis vaccine at less than 42 days of age of the mammal and administering at least a second dose of the diphtheria/tetanus/pertussis vaccine, wherein the second dose and or any subsequent doses is administered less than 28 days after the preceding dose when the mammal is less than 175 days of age; and (3) administering at least one dose of the diphtheria/tetanus/pertussis vaccine at less than 42 days of age of the mammal and administering a total of at least four doses of the diphtheria/tetanus/pertussis vaccine prior to the age of 112 days of the mammal; wherein the further administration reduces at least one measure in the group consisting of incidence, prevalence, frequency, and severity of at least one chronic immune mediated disorder and or of at least one surrogate marker of the disorder in a population and or subpopulation of the mammals.

In the method above, further reduction in the measures may be induced by further administering to the mammal at least one pharmaceutically acceptable dose of at least one pharmaceutically acceptable immunogen selected from the group consisting of an non-pediatric immunogen, hepatitis B immunogen, hemophilus influenza immunogen, a measles/mumps/rubella immunogen, and polio immunogen, where the further administration is according to at least one method from the group consisting of; (1) administrating at least one dose of the immunogen at less than 42 day of age of the mammal; (2) administering at least one dose of the immunogen, the dose comprising at least a second dose, wherein the second dose and or any subsequent doses is administered less than 28 days after the preceding dose when the mammal is less than 175 days of age; and (3) administrating at least four doses prior to the age of 112 days of the mammal.

The methods of the present invention also provide a method for pediatric immunization against at least two infectious diseases, comprising administering at least one pharmaceutically acceptable dose of at least one pediatric vaccine to a mammal of at least 42 days of age, the improvement comprising further administering to the mammal of at least 28 days of age but less than 175 days of age at least one pharmaceutically acceptable dose of at least one pharmaceutically acceptable immunogen wherein a total of at least 4 separate pharmaceutically acceptable doses of at least one pharmaceutically acceptable immunogen from the group consisting of a diphtheria/tetanus/pertussis immunogen, hepatitis B immunogen, hemophilus influenza immunogen, measles/mumps/rubella immunogen, polio immunogen, and a non-pediatric immunogen are administered to the mammal during the ages described above wherein at least 2 of the at least 4 doses are provided prior to the age of 112 days of the mammal wherein the further administration reduces at least one measure in the group consisting of incidence, prevalence, frequency, and severity of at least one chronic immune mediated disorder and or of at least one surrogate marker of the disorder in a population and or subpopulation of the mammals.

The methods of the present invention also provide a method for pediatric immunization against at least two infectious diseases, comprising administering at least one pharmaceutically acceptable dose of diphtheria/tetanus/pertussis vaccine and at least one pharmaceutically acceptable dose of hemophilus influenza vaccine to a mammal of at least 42 days of age, the improvement comprising further administering to the mammal at least one pharmaceutically acceptable dose of at least one or both in the group consisting of diphtheria/pertussis/tetanus vaccine and hemophilus influenza vaccine where the further administration is according to at least one method from the group consisting of; (1) administrating at least one dose of both the diphtheria/pertussis/tetanus vaccine and the hemophilus influenza vaccine at less than 42 days of age of the mammal, and at least a second dose of at least one said vaccine prior to 42 days of age; (2) administering at least one dose of both the diphtheria/tetanus/pertussis vaccine anvacci hemophilus influenza vaccine at less than 42 days of age of the mammal and administering at least a second dose of both vaccines, wherein the second dose and or any subsequent doses is administered at less than 42 days after the preceding dose when the mammal is less than 175 days of age; and (3) administering at least one dose of both the diphtheria/tetanus/pertussis vaccine and the hemophilus influenza vaccine at less than 42 days of age of the mammal and administrating at least four doses prior to the age of 112 days of the mammal for the diphtheria/pertussis/tetanus vaccine and or the hemophilus influenza vaccine; wherein the further administration reduces at least one measure in the group consisting of incidence, prevalence, frequency, and severity of at least one chronic immune mediated disorder and or of at least one surrogate marker of the disorder in a population and or subpopulation of the mammals. The mammals are preferably not hyper sensitive to the agent.

The methods of the present invention also provide a method for pediatric immunization against at least two infectious diseases, comprising administering at least one pharmaceutically acceptable dose of at least one pharmaceutically acceptable immunogen in a group comprising an diphtheria/tetanus/pertussis immunogen, polio immunogen, hepatitis B immunogen, hemophilus influenza immunogen, non-pediatric immunogen, and a measles/mumps/rubella immunogen to a mammal after 112 days of age but prior to 724 days of age, the improvement comprising further administering the immunogen to the mammal prior to the age of 112 days at least one pharmaceutically acceptable dose containing a greater amount of the immunogen then at least one doses administered after 112 days of age but prior to 724 days of age of the mammal, wherein the further administration reduces at least one measure in the group consisting of incidence, prevalence, frequency, and severity of at least one chronic immune mediated disorder and or of at least one surrogate marker of the disorder in a population and or subpopulation of the mammals. The greater amount may comprise a supraimmunogenic dose. The mammals are preferably not hypersenitive to said immunogen.

The methods of the present invention also provide a method for pediatric immunization against at least two infectious diseases, comprising administering at least one pharmaceutically acceptable dose of an non-whole cell pertussis vaccine to a mammal at least 42 days of age but prior to 724 days of age, the improvement comprising further administering to the mammal at least one pharmaceutically acceptable dose of at least one pharmaceutically acceptable immunogen selected from the group consisting of an diphtheria/tetanus immunogen, non-whole cell pertussis immunogen, whole cell pertussis immunogen, polio immunogen, hemophilus influenza immunogen, measles/mumps/rubella immunogen and a non-pediatric immunogen where the administration is according to at least one method from the group consisting of; (1) administrating at least one dose of the immunogen at less than 42 days of age of the mammal; (2) administering at least one dose of the immunogen, the dose comprising at least a second dose, wherein the second dose and or any subsequent doses is administered less than 28 days after the preceding dose when the mammal is less than 175 days of age;and (3) administrating at least four doses prior to the age of 112 days of the mammal; wherein the further administration reduces at least one measure in the group consisting of incidence, prevalence, frequency, and severity of at least one chronic immune mediated disorder and or of at least one surrogate marker of the disorder in a population and or subpopulation of the mammals.

The methods of the present invention also provide a method for pediatric immunization against at least two infectious diseases, comprising administering at least one pediatric vaccine to a mammal of at least 42 days of age, the improvement comprising further administering to the mammal at least one pharmaceutically acceptable dose of at least one pharmaceutically acceptable vaccine selected from the group consisting of a combined vaccine containing at least diphtheria, tetanus, pertussis, and hemophilus influenza immunogens, and a combined vaccine containing at least diphtheria, tetanus, pertussis, and hepatitis B immunogens, where the administration is according to at least one method from the group consisting of (1) administrating at least one dose of the vaccine at less than 42 days of age of the mammal; (2) administering at least one dose of the vaccine, the dose comprising at least a second dose, wherein the second dose and or any subsequent doses is administered less than 28 days after the preceding dose when the mammal is less than 175 days of age;and (3) administrating at least four doses prior to the age of 112 days of the mammal; wherein the further administration reduces at least one measure in the group consisting of incidence, prevalence, frequency, and severity of at least one chronic immune mediated disorder and or of at least one surrogate marker of the disorder in a population and or subpopulation of mammals.

The methods of the present invention also provide a method for pediatric immunization against at least two infectious diseases and tolerizing against at least one antigen, comprising administering at least one pharmaceutically acceptable dose of at least one pediatric vaccine to a mammal of at least 42 days of age and administering at least one tolerogen to the mammal, the improvement comprising further administering to the mammal at least one pharmaceutically acceptable dose of at least one pharmaceutically acceptable immunogen selected from the group consisting of an diphtheria/tetanus/pertussis immunogen, hemophilus influenza immunogen, a measles/mumps/rubella immunogen, polio immunogen, and an non-pediatric immunogen where the further administration is according to at least one method from the group consisting of;
(1) administrating at least one dose of the immunogen at less than 42 day of age of the mammal; (2) administering at least one dose of the immunogen, the dose comprising at least a second dose, wherein the second dose and or any subsequent doses is administered less than 28 days after the preceding dose when the mammal is less than 175 days of age;and (3) administrating at least four doses prior to the age of 112 days of the mammal; wherein the further administration reduces at least one measure in the group consisting of incidence, prevalence, frequency, and severity of at least one chronic immune mediated disorder and or of at least one surrogate marker of the disorder in a population and or subpopulation of the mammals.

The methods of the present invention also provide a method for pediatric immunization against at least two infectious diseases, comprising administering at least one pharmaceutically acceptable dose of at least one pediatric vaccine to a mammal of at least 42 days of age, the improvement comprising further administering to the mammal at least one pharmaceutically acceptable supraimmunogenic dose of at least one pharmaceutically acceptable vaccine prior to the age of 112 days of the mammal, wherein the further administration reduces at least one measure in the group consisting of incidence, prevalence, frequency, and severity of at least one chronic immune mediated disorder and or of at least one surrogate marker of the disorder in a population and or subpopulation of the mammals.

The at least one supraimmunogenic dose, may comprise at lease a second dose, wherein the second dose and or any subsequent supraimmunogeic doses may be administered less than 28 days after the preceding dose when the mammal is less than 175 days of age.

The methods of the present invention also provide a method for pediatric immunization against at least two infectious diseases, comprising administering at least one pharmaceutically acceptable dose of at least one pediatric vaccine to a mammal of at least 42 days of age, the improvement comprising further administering to the mammal at least one pharmaceutically acceptable dose of at least one pharmaceutically acceptable immunogen to the mammal prior to the age of 8 days and administering at least one pharmaceutically acceptable dose of at least one pharmaceutically acceptable immunogen to the mammal at least 11 days of age but less than 26 days of age wherein the further administrations reduce at least one measure in the group consisting of incidence, prevalence, frequency, and severity of at least one chronic immune mediated disorder and or of at least one surrogate marker of the disorder in a population and or subpopulation of the mammals.

In the method above, an additional immunization may be made comprising administering at least one pharmaceutically acceptable dose of at least one pharmaceutically acceptable immunogen at least 11 days but less than 26 days after the last dose of the immunogen proceeding 26 days of age of the mammal. At least one pharmaceutically acceptable dose of at least one pharmaceutically acceptable immunogen may be administered at least 11 days but less than 26 days after the additional immunization.

The methods of the present invention also provide a method for pediatric immunization against at least two infectious diseases, comprising administering at least one pharmaceutically acceptable dose of at least one pharmaceutically acceptable immunogen to a mammal, the improvement comprising further administering at least a second pharmaceutically acceptable dose of at least one pharmaceutically acceptable immunogen, wherein the second dose and or any subsequent doses is administered less than 28 days after the preceding dose where the second and or any subsequent doses may or may not contain the same immunogens and or amounts of the immunogens as any other dose. Each separate dose may include at least one immunogen administered during a range including 0–78 hours or any range or value therein. Wherein the further administration reduces at least one measure in the group consisting of incidence, prevalence, frequency, and severity of at least one chronic immune mediated disorder and or of at least one surrogate marker of the disorder in a population and or subpopulation of the mammals.

In the method above total number of separate doses may be at least 4 prior to 112 days of age of the mammal.

The methods of the present invention also provide a method for pediatric immunization against at least two infectious diseases, comprising administering at least one pharmaceutically acceptable dose of hepatitis B vaccine to a mammal of at least 42 days of age, the improvement comprising further administering to the mammal at least one pharmaceutically acceptable dose of the hepatitis B vaccine according to at least one method in the group consisting of (1) administrating at least 3 doses of the vaccine at less than 56 days of age of the mammal; (2) administering at least one dose of the vaccine, the dose comprising at least a second dose, wherein the second dose and or any subsequent doses is administered less than 28 days after the preceding dose when the mammal is less than 175 days of age; and (3) administrating at least four doses prior to the age of 112 days of the mammal, wherein the further administration reduces at least one measure in the ground consisting of incidence, prevalence, frequency, and severity of at least one chronic immune mediated disorder and or of at least one surrogate marker of the disorder in a population and or subpopulation of the mammals.

A list of definitions is included below that may be used to reiterate the meaning of terms used herein that are already implied in the methods described herein.

The ability of an immunization program to substantially reduce the incidence or severity of an immune-mediated disorder is preferably determined relative to a standard immunization protocol. The following three schedules are preferred standards:

| | Schedule | | |
|---|---|---|---|
| Week | 1 | 2 | 3 |
| 0 | x | x | HepB |
| 2 | x | x | x |
| 4 | x | x | HepB |
| 6 | DTP, Polio, HepB, HiB | x | x |
| 8 | x | DTP, Polio, HepB, HiB | DTB, Polio, Hib |
| 10 | DTP, Polio, HepB, HiB | x | x |
| 12 | x | DTP, Polio, HepB, HiB | DTP, Polio, HiB |
| 14 | DTP, Polio, HepB, HiB | x | x |
| 16 | x | DTP, Polio, HepB, HiB | DTP, Polio, HiB |
| 60 | MMR | MMR | MMR |

MMR: Measles, Mumps, Rubella
HepB: Hepatitus B
HiB: Hemophilus Influenza
x: No administration Preferably, a statistically significant ($p \leq .05$) reduction of at least 10% is seen, relative to control employing one of these three schedules or relative to untreated controls. More preferably, the reduction is greater, i.e., at least 20% or at least about 50%.

The at least one surrogate marker may be selected from the group consisting of an autoantibody, an autoreactive lymphocyte, a biochemical marker of tissue destruction, an biochemical marker of abnormal secretion from an internal body organ, an positive skin reaction to an immunological challenge which indicates immunological hypersensitivity, and an elevated level of antibodies that correlate with hypersensitivity. The abnormal secretion from an internal body organ may be abnormal insulin secretion.

The chronic immune mediated disorder may be selected from a hyperactive immune response and an immune mediated cancer, as further described herein. In a preferred embodiment, at least one chronic immune mediated disorder in question is diabetes mellitus.

The at least one pharmaceutically acceptable immunogenic agent preferably further comprises a pharmaceutically acceptable carrier. The least one pharmaceutically acceptable immunogenic agent may comprise at least one immunogen in any, some or all the 5 classes of immunogens described herein. The immunogens may be selected from the group consisting of living and non living immunogens. Non living immunogens may comprise recombinantly produced immunogens. The non-pediatric immunogen is an immunogen not routinely given to the mammal prior to 112 days of age, in a modern developed country in 1992, and includes imuunogens described herein.

The hepatitis B vaccine may be recombinant or produced from blood products. The polio immunogen may be a live and or killed immunogen. The polio immunogen may also include a trivalent immunogen such that the polio immunogen may induce in mammals antibodies reactive to 3 serotypes of polio virus. The hemophilus influenza immunogen may be a conjugated and or unconjugated immunogen. The pertussis immunogen may be selected from the group consisting of a non-whole cell and a whole cell immunogen. The non-whole cell immunogen may included acellular pertussis immunogens. At least one in the group consisting of a diphtheria/tetanus/pertussis immunogen, hepatitis B immunogen, hemophilus influenza immunogen, and a polio immunogen may further comprises a depot type adjuvant. The term age refers to time after delivery. Delivery and birth are used to mean the same thing in this paper.

The pharmaceutically acceptable dose of the at least one pharmaceutically acceptable immunogen may be 0.01–10,000 micrograms of immunogen per kilogram body weight of the mammal as described herein.

The mammal in the method may be a human. The human may live in a modern developed nation and where pediatric immunogens comprises a diphtheria/tetanus/pertussis immunogen, hepatitis B immunogen, hemophilus influenza immunogen, polio immunogen, and a measles/mumps/rubella immunogen. The mammals may be healthy and not in at least one group consisting of premature mammals before the natural gestational period, mammals suffering from diarrhea, mammals suffering from an infection, and mammals suffering from a fever.

The methods described herein may be a step or steps in a method or methods that prevents or reduces at least one measure in the group consisting of incidence, prevalence, frequency, and severity of at least one chronic immune mediated disorder and or of at least one surrogate marker of the disorder in a population or subpopulation of the mammals. The disorder may include diabetes mellitus.

In a preferred embodiment, an immunogen designed to reduce the incidence of a chronic immune mediated disorder can be given starting during the first week of life and continuing as frequently as practically possible and safe to do so for at least the first 8 to 32 weeks (as in 8, 9, 10, 11, 12, 13, 14, 15, 16, 17, 18, 19, 20, 21, 22, 23, 24, 25, 26, 27, 28, 29, 30, 31 and 32). For an agent being added to a immunization schedule in hopes of preventing an infectious disease the agent preferably may be administered as above or if immunization can not be performed beginning during the first 6 weeks of life then one should avoid high doses, preferably using no administrations from 6 weeks to 28 weeks or more of life.

Vaccination schedules can be as short as 3 shots and as infrequent as every other week and still be effective. Example 1, as non-limiting example, shows that only 3 vaccinations with a single mild agent, anthrax vaccine, can cause a profound reduction in diabetes. Increasing the number of vaccination increases the effect when using a mild agent like the anthrax vaccine as seen by the improvement from Example 1 to Example 2. Even fewer injections or less frequent injection protocols may also be used, especially when using a strong agent like the DTP vaccine or higher doses.

VI. Screening Methods for Determination of Suitable Immunogenic Agents and Dosing The present invention also provides methods for screening potentially pharmaceutically acceptable immunogenic agents and or dosing regiments for their suitability and effectiveness in preventing at least one chronic immune mediated disorder and at least one infectious disease. One skilled in the art can perform any of the following screening methods or as few as desired to determine information sought by the investigator. The preferred order of performing the screening methods is listed below, however, one can perform the methods in any order that best suits the investigator. The term potentially pharmaceutically acceptable implies that the agents are not associated with any toxicities, at doses that they are being used in the screening methods, that would prohibit their use.

The methods may be adopted to screen for the ability of a immunization schedule containing one or more potentially pharmaceutically acceptable immunogens and one or more potentially pharmaceutically acceptable immune modulators to prevent both chronic immune mediated diseases and infectious diseases. Immune modulators may be substituted for one or more immunogens in the following methods where applicable. Appropriate doses of immune modulators to use can be calculated from references cited herein, references found in Medline/Index Medicus or other suitable database, and for new immune modulators one can use doses by weight approximating those used for immunogens. Suitable screening methods, such as described herein, will allow one skilled in the art to develop effective compounds, and determine optimal dosing regiments. Such, methods may include at least one of: determining if the agent is an immunogen; determining if said immunogen is effective in preventing disease; determining an safe and effective range or if the range does not exist; determining if said agent modulates at least one chronic immune mediated disorder in mammals that already receive immunogens early in life to protect against infectious diseases; determining a safe and effective agent and or dosing regiment; and determining if said safe and effective agent and/or dosing regiment as part of an pediatric immunization protocol also provides protection against at least one infectious disease.

The preferred method for finding immunogens suitable for use in the present invention is to start with an extract derived from at least one foreign organism, such as a bacteria, virus, fungus, insect, plant, allogenic or xenogenic animal. A simple screening test for determining if an agent is an immunogen is to inject the agent subcutaneously in an mammal such as a mouse and looking for the development of inflammation at the injection sight as well as the development of antibodies to the agent. The injection site can be in a paw pad, or an ear for example. Mice that appear to have an immune response can have blood drawn and checked for antibodies to the agent. An ELISA is an simple assay that can be used to screen many animals for antibodies very quickly. Delayed type hypersensitivity assay can be performed for determining if the agent induces a cellular immune response. Controls can be made by using animals that receive only the vehicle used to suspend the potential immunogen in question.

In vitro assays can also be developed to screen for potential immunogens. These assays are best suited for screening immune modulators like lymphokines, and certain monoclonal antibodies believed to have immune regulatory effects. As a non-limiting example, splenocytes, thymocytes or lymphocytes can be cultured in a 96 well place with supportive media. Uptake of tritium labeled thymidine 48–72 hours after the addition of an potential immunogen can suggest the activation and proliferation of immune mediator cells, suggesting that said agent is an immunogen.

Once an agent has been confirmed to be an immunogen, a screening study can be performed to determine its effectiveness in preventing at least one chronic immune mediated disorder. High doses of the immunogen are recommended initially so that an effect due to using too low a dose is not missed. Preferred starting dose is 1 to 2 mg/kg body weight. A preferred method is to give autoimmune prone mammals intraperitoneal injections with the agent starting within 10 days of birth and continuing every 2 weeks for 4 injections. Control animals can be injected with phosphate buffered saline or any vehicle that the immunogen is dissolved in. Blood can be drawn from the mammals and checked for the presence of hyperglycemia in diabetic prone mammals or autoantibodies in autoimmune prone mammals that develop antibody mediated disease. Tissue from the study mammals can be removed and histology can be performed to determine if the tissue is affected by chronic immune mediated disorders. Non-limiting examples include pancreatic islet cells in diabetes prone mammals or gastric fundi in mammals prone to develop autoimmune gastritis. Histology is generally a less sensitive assay than ELISA assays for autoantibodies or blood glucose for diabetes. All results in the treated group can be compared to the control mammals.

Several screening methods lend themselves very well to determining if the agent has effects on inhibiting chronic immune mediated disorders. Non-obese diabetic (NOD) mice or Bio Breeding (BB) rats can be used to screen an agent for effectiveness in preventing diabetes. Mice can be injected as above and blood drawn to check for hyperglycemia at monthly intervals through the first 6 months of life. Ten or more female NOD mice will give an quick first approximation of an effect. Detailed methods are provided in examples 1 and 2 below. Other possible methods of screening agents for their effectiveness in preventing chronic immune mediated diseases beside diabetes also exist. Cyclosporine induced autoimmunity, e.g., as demonstrated in example 3, is one method for screening agents for their ability to inhibit organ specific autoimmune disease like gastritis. Different strains of mice are more prone to develop certain autoimmune diseases when they are altered then others (Kojima and Prehm, 1981). One can pick a strain depending on what disease one wants to look at. Blood can be screened for autoantibodies using ELISA assays as described in example 3 below. There is a large number of ELISA assays that have been published in the scientific literature and these can be found looking through index medicus or a similar computer file referencing autoantibodies and the particular autoantigen or organ system one wants to study. See also Ausubel, supra, Coligan, supra, Harlow, supra.

Agents that have been shown to effectively inhibit chronic immune mediated disorders at high doses may be screened to determine what doses if any may be safely administered to an mammal. Routine toxicology tests, as those requested by a regulatory agency such as the FDA, can be performed at varying doses to determine an safe dosing range. Non limiting examples of such tests include mutagenesis, carcinogenesis, acute toxicity on vital organs such as the kidneys, lung, heart, liver, and brain, chronic toxicity of the organs, as well as defining a lethal dose.

The present invention also pertains to a method to screen vaccines to determine their propensity to induce diabetes mellitus or chronic immune mediated disorders like autoimmune diseases. A group of autoimmune prone mammals may be given an agent in the first months of life, as an non-limiting example, a less strong immunogen, to reduce the incidence of autoimmunity in those mammals. A diphtheria/tetanus vaccine is a preferred embodiment and the dose used is expected to reduce the incidence of autoimmunity by 50%–75% compared to untreated mammals, but should preferably not completely inhibit autoimmunity. A second group of autoimmune prone mammals should receive the same immunogen and dose, but should receive the vaccine in question at approximately 2 months of age or later, with 2 months preferred. The incidence of diabetes or autoimmunity should be noted in each group. Safety should be assessed by determining the incidence or prevalence of disease in the two groups. An example of the method is demonstrated in example 2, where the diphtheria tetanus vaccine is given to 2 groups of NOD mice but one group also received an additional administration of pertussis vaccine at approximately 2 months of age. The later group developed a higher incidence of diabetes suggesting that pertussis vaccine can have a toxic effect by inducing diabetes. Non limiting examples of other possible autoimmune prone mammals that can be used in the screening method include cyclosporine treated mice, see example 3 below, and day 3 thymectomized mice.

The mammals in the previous methods should be raised in an pathogen-free environment as a preferred embodiment. A non limiting example of an suitable environment includes housing animals where the caging, bedding, food and water are all autoclaved, the cage has filters to prevent pathogens from entering the cage. As an preferred environment the cage should only be opened under a laminar flow hood equipped with filters to trap pathogens. The use of an pathogen free environment prevents mammals from exposure to natural immunogens that may effect the interpretation of the results.

The present invention also pertains to a method to screen potentially pharmaceutically acceptable immunogens to determine their propensity to modulate at least one chronic immune mediated disease in mammals that live in open environments, as opposed to pathogen free environments, which receive extensive exposure to both pharmaceutically acceptable and natural immunogens early in life. In said method, mammals should receive at least one vaccine during the pediatric age range, as defined herein where the agent is capable of preventing an infectious disease caused by an infectious agent or capable of inducing neutralizing antibodies to the infectious agent. In the screening method the dosing regiment to prevent at least one chronic immune mediated disorder and at least one infectious agent is termed an immunization protocol.

The screening method may involve administering at least one potentially pharmaceutically acceptable dose of at least two potentially pharmaceutically acceptable immunogenic agents comprising at least one potentially pharmaceutically acceptable pediatric immunogen and at least one agent selected from the group consisting of a second pediatric immunogen and a non-pediatric immunogen, for the ability to modulate the development of at least one chronic immune mediated disorder and or of at least one surrogate marker of the chronic immune mediated disorder in a population and or subpopulation of mammals. The method comprising administrating to at least one treatment group of at least one mammal at risk for at least one chronic immune mediated disorder at least one treatment dose of immunogenic agents according to a treatment administration schedule. The at least one treatment dose may comprise at least a first treatment dose of at least one of the immunogenic agents administered prior to an age of 56 days of the mammal.

One or more control groups of at least one mammal may be defined optionally. The control groups may receive at least one control dose which contains at least one potentially pharmaceutically acceptable pediatric vaccine and has at least one modification selected from the group consisting of: (i) lacking at least one immunogenic agent/adjuvant than as is provided in the treatment schedule; (ii) including at least one immunogenic agent/adjuvant than as is provided in the treatment schedule; (iii) including a higher dose of at least one immunogenic agent/adjuvant than as is provided in the treatment schedule; (iv) including a lower dose of at least one immunogenic agent/adjuvant than as is provided in the treatment schedule; (v) including at least one additional dose of at least one immunogenic agent/adjuvant than as is provided in the treatment schedule; (vi) lacking at least one dose of at least one immunogenic agent/adjuvant than as is provided in the treatment schedule; (vii) including at least one dose of at least one immunogenic agent/adjuvant at a later time than the immunogenic agent/adjuvant is administered in the treatment schedule; (viii) including at least one dose of at least one immunogenic agent/adjuvant at an earlier time than the immunogenic agent/adjuvant is administered in the treatment schedule; and (ix) no modifications from the treatment schedule wherein at least one measure in the group consisting of incidence, prevalence, frequency, and severity of at least one chronic immune mediated disorder and or of at least one surrogate marker of the disorder can be/has been determined in the control group. The term immunogenic agent in this paragraph refers to an immunogen that is unbound or administered with a particular pharmaceutical carrier at a definable ratio as described herein. The terms treatment schedule and treatment administration schedule are used interchangeably herein.

Participants may be screened to determine the modulation of development of the at least one chronic immune mediated disorder by at least one of the treatment administration schedules. The determining step may comprise ascertaining at least one measure from the group consisting of incidence, prevalence, frequency and severity of at least one chronic immune mediated disorder and or of at least one surrogate marker of the disorder in at least one mammal in at least one treatment group and optionally the same measures in at least one mammal in the one or more control groups. If the occurrence of the measures is at an acceptable level as in a non limiting example of no occurrences, an incidence or prevalence of zero, then the analysis may not require comparison with the optionally defined one or more control groups to demonstrate efficacy.

The terms treatment group and control group may be used interchangeably at times if all conditions hold, such that a control group in one screening trial may be the treatment group in the next or visa versa. As the preferred embodiment the optional one or more control group should contain mammals that receive an currently recommended immunization schedule as in the non limiting examples of the schedules recommended by the Centers for Disease Control, CDC, and or the American Academy of Pediatrics.

One may define the optional one or more control groups of at least one mammal and determine the measures in the control group. Comparison of data from the one or more control groups to data from the at least one treatment group may be performed to determine if the treatment schedule can modulate at least one measure in at least one chronic immune mediated disorder. In a preferred embodiment the size of the groups should allow determination of statistical significance during an acceptable period of time. Any statistical method that is deemed appropriate for the trial design by one skilled in the art may be acceptable.

In order to select an appropriate size of the treatment and control groups it is first helpful to know the incidence/prevalence/frequency/severity of the chronic immune mediated disorder and or surrogate marker of the disorder in the population one is studying, preferably in age groups as in the non limiting example of children below 15 years of age. Given the desired change in incidence of disease one hopes to be able to detect, and the statistical test one is employing, one can determine the size of a population needed for the at least one treatment group and the one or more control groups to demonstrate statistical significance.

As an non-limiting example one can estimate the incidence of diabetes in a control group of caucasian children from European decent under 15 years of age by knowing their immunization schedule and using data from example 4. Using an estimate of the desired level of reduction in the parameter one wants to be able to detect and knowing the power of the statistical method one is using one can estimate the population size one needs to use in the study. A preferred embodiment is an minimal reduction of at least 5% or more or the equivalent of a statistical P value of 0.05 or less.

It is preferred to perform the screening method in a developed country where the exposure to pathogens is reduced during the first year of life. Developed countries have expensive water purification and sewer systems that reduce an infant's exposure to the pathogens. The method should preferably allow one skilled in the art to determine if the treatment administration schedule prevents, induces, or has no affect over the currently recommended immunization schedule.

Developed countries may include the United States, Canada, and the European nations listed in the table pertaining to example 4. A country may be considered developed if it has both a per capita income greater than or equal to any of the above countries, and nationwide water purification systems as well as sewage treatment systems which equal or surpass that in the above nations.

The mammals of the screening methods may include as non limiting examples rodents such as NOD mice and BB rats, and primates such as humans.

A human study population will preferably contain individuals who are at risk for development of the chronic immune mediated disorder. For example, in the case of diabetes mellitus, it will preferably include at least 25% Caucasians of European descent. Caucasians of European descent have a high rate of diabetes and certain autoimmune diseases as compared to other groups like Japanese and this invention shows that occurrence of diabetes in European caucasians is sensitive to vaccination.

One or more groups, as in controls or treatment groups, may receive pediatric immunization against at least 4 out of the group of diseases comprising pertussis, diphtheria, tetanus, hemophilus influenza, hepatitis B.

The screening method may be retrospective, prospective or contain data derived both retrospectively and prospectively. individual mammals may be placed in a particular study group based a selection process that is either random, non random or both, however random selection is the preferred method. Participants, their families, and researchers may be either blinded, unblinded or both to the immunization schedule. The endpoints of the screening method may be the diagnosis of at least one chronic immune mediated disorder and or surrogate marker of the disease in an individual. The preferred embodiment is to use at least one disease that develops early in life, is relatively frequent, and has a clearly defined endpoint with the non limiting example being type I diabetes mellitus.

The term at least one chronic immune medicated disorder may include at least 2 classes of disease in the group of classes consisting of diabetes mellitus, a conventional organ specific autoimmune disease, a neurological disorder, a rheumatic/connective tissue disorder, an autoimmune cytopenia, an allergy/asthma, an immune mediated cancer.

The term at least one chronic immune mediated disorder may include at least two diseases from at least one class of diseases from the group of classes consisting of diabetes mellitus, a conventional organ specific autoimmune disease, a neurological disorder, a rheumatic/connective tissue disorder, an autoimmune cytopenia, an allergy/asthma, and an immune mediated cancer. By using the combination of several diseases as an end point the number of participants needed to show a statistical effect is reduced and the time to detect an effect is reduced. Prior to this invention it was not accepted that pharmaceutical acceptable doses of pharmaceutically acceptable immunogenic agents could prevent one chronic immune mediated disorder much less several classes.

A retrospective or historical method of screening, as in a study or trial, may be performed to determine whether a pharmaceutically acceptable amount of a pharmaceutically acceptable immunogen may prevent, induce or is not associated with an increase in diabetes or autoimmunity. The method may include at least one control group and at least one treatment group as stated herein. In a non limiting preferred embodiment it is often easier to compare people in different countries because most people in a given country tend to receive the same vaccines so it is hard to get an unbiased grouping of those who received and those that did not receive vaccine. Governments' decisions on whether to promote immunization of the citizens with a particular vaccine like BCG is often ambiguous. Thus one can have a situation where genetically and culturally similar people live on opposite sides of a national border and one group of citizens receives a particular vaccine and another nationality does not receive the vaccine or receives it at a different age. An non limiting example of such a case is the BCG vaccine as described in example 4.

Another non-limiting example of using retrospective data to screen an pharmaceutically acceptable immunogen for the ability to modulate a chronic immune mediated disease is to study the effect of changing an immunization schedule on the incidence of disease. In places where the immunization schedule has changed as in the case of Sweden, see example 4 discussed herein, one skilled in the art can study the effect of the change on the development of at least one chronic immune mediated disorders. The incidence/prevalence/frequency/severity of the at least one disorder and or surrogate marker of the at least one disorder prior to the change may be determined retrospectively and or prospectively and the parameters of the at least one disorder after the change may be determined prospectively and or retrospectively.

One skilled in the art may also perform prospective screening methods. As a non-limiting example mammals in a treatment group may receive one immunization schedule and mammals in a control group may receive a different immunization schedule as described above. The incidence/ prevalence/ frequency/severity of at least one chronic immune mediated disorder and or at least one surrogate marker of the at least one disorder is determined prospectively in each group. An non limiting alternative to the example is where the data from one group may be determined retrospectively and the data from another is determined prospectively.

The screening method may be designed to control for and or estimate the effects on at least one mammal in at least one treatment/control group from at least one confounding variable in the group consisting of receiving breast feeding versus bottle feeding prior to 12 months of age, receiving antibiotics during the first 12 months of life, the maternal age at birth, the presence of a chronic immune mediated disorder in the mother/father/a close relative, maternal infections while the mammal was in utero, infections during the first 12 months of life, size of the mammal at birth, gestational age of the mammal at birth, exposure of the mammal to BCG vaccine/naturally acquired mycobacterium, and exposure to vaccines.

Studies may give misleading results on a vaccine's safety if one does not take into consideration that having a disease like measles may be associated with a higher incidence of a chronic immune mediated disorder than receiving the vaccine for the disease. A vaccine may induce chronic immune mediated disorders but at a lower rate than the infectious agent it protects against.

One may design the trial to control for and or determine the difference in at least one chronic immune mediated disorder between a group which received a vaccine but did not develop the infectious disease which the vaccine protects and a group that did not receive the vaccine but also did not develop the infectious disease. The difference in at least one chronic immune mediated disorder may include at least one measure in the group consisting of incidence, prevalence, frequency, and severity of at least one chronic immune mediated disorder and or of at least one surrogate marker of the at least one disorder. Type I diabetes mellitus is the preferred chronic immune mediated disease to study for reasons mentioned above.

The optional one or more control groups may receive an administration of at least one potentially pharmaceutically acceptable pediatric vaccine prior to the age of 56 days of the at least one mammal.

The treatment group may receive at least one dose of at least one immunogenic agent/adjuvant not administered to at least one control group.

The term modulate may include preventing or enhancing as in inducing an chronic immune mediated disorder. The screening trial may be designed to determine if the treatment administration schedule will prevent and or reduce the severity of at least one chronic immune mediated disorder. Alternatively the screening trial may be designed to determine if the treatment administration schedule will induce and or enhance the severity of at least one chronic immune mediated disorder.

A potentially pharmaceutically acceptable immunogen may be any immunogen discussed herein that meets the definition of potentially pharmaceutically acceptable. Preferably the immunogen is administered with a carrier as discussed herein. The term pharmaceutically acceptable pediatric immunogen may include one member selected from the group comprising a diphtheria/tetanus/pertussis, hepatitis B, polio, hemophilus influenza vaccine, and measles/mumps/rubella immunogen. In a preferred method the control and the treatment administration schedule may differ by one or more immunogens other than a BCG/small pox immunogen.

The immunogen may be administered by any method that is effective and is pharmaceutically acceptable as described herein. Preferably the administration should be by at least one method described in section V of this text.

Upon completion and or partial completion of the screening method, data may then be used for determining/verifying the existence of an effective immunization dose/dosing schedule for modulating at least one chronic immune mediated disorder, for at least one dose. Data from the screening method may be processed by a processor or alternatively manuallaly. An effective dose may be calculated that causes a difference in at least one measure in the group consisting of incidence, prevalence, frequency, and severity of the chronic immune mediated disorder and or of at least one surrogate marker of the disorder in at least one mammal in at least one treatment group compared to at least one measure in at least one mammal in at least one control group. In a situation where the control administration is not associated with causing a reduction in at least one said measure of the chronic immune mediated disorder(s) studied the control group comprises at least one of the modifications (i)–(viii), and the treatment causes at least statistically significant ($p=0.05$) 5% improvement. In a situation where the control administration is associated with causing a reduction in at least one measure of the chronic immune mediated disorder(s) studied, the control group comprises the modifications (i)–(ix) and the difference is not statistically significant or the treatment shows a benefit.

One can further analyze the data to determine/verify if an immunization dose/dosing schedule provides safety and efficacy in modulating at least one chronic immune mediated disorder wherein efficacy may be determined as discussed herein, and an effective dose may be safe for the mammals. Safety may be evaluated by determining if the dose/dosing schedule is pharmaceutically acceptable as described herein.

The data may be analyzed even further to determine/ verify if an immunization dose/dosing schedule provides safety, efficacy in modulating at least one chronic immune mediated disorder and provides protection against at least one infectious disease. At least one of safety and efficacy may be determined as discussed herein and protection against infectious diseases may be determined as discussed herein also.

One may use several different methods to determine if an mammal develops protection against at least one infectious disease for which the at least one mammal received immunization against in the pediatric age as defined earlier. In an non limiting example one can determine the incidence/ prevalence/frequency/severity of the at least one infectious disease in the at least one treatment/control group in question and determine if the group received adequate protection from the at least one infectious disease. In an alternative method members of the group in question may be screened for the development of a protective level of antibodies to the causative infectious agents. As a non limiting example the level of protection may be compared to at least one of the following: (i) a group that received no protection/ immunization, (ii) a group that receives a recommended immunization schedule, (iii) an rate that is deemed acceptable by professionals in the field as in those affiliated with the Centers for Disease Control, the American Academy of Pediatrics and or the FDA.

The size of a group needed to determine if an dosing schedule provides protection against at least one infectious agent is generally smaller than that needed to detect an effect on reducing a chronic immune mediated disorder because the incidence of the former diseases are generally higher than the later diseases and the former may occur earlier in life than the later. If the end point of the study is the development of protective or neutralizing antibodies two hundred mammals or less may be sufficient. The trial preferably will utilize any statistical method that is acceptable and is congruent with the study design.

The term processor as used herein refers to any mechanical or electrical computing device as in the non limiting examples of a computer or calculator.

A preferred method for screening is to perform a prospective randomized blinded clinical trial in an industrialized nation where the majority of the participants are caucasians from European decent. The controls should receive an vaccination schedule according to the CDC and the treatment group receive a method of immunization described in section V. The endpoint of the trial is preferably diabetes or the sum of several chronic immune mediated disorders that include diabetes. A large population, approximately 60,000 volunteers or more is preferred and the trial should be followed for approximately 10 years or longer to generate strong data on the effect.

A smaller group of participants, several thousand, with high risk of developing chronic immune mediated disorders because of family history or genetic screening, may be used in an initial trial to see if an given immunization schedule may have an effect in modulating chronic immune mediated disorders. Participants may be screened for surrogate markers like autoantibodies before disease is detected in order to get a predicator of how effective the method may be in modulating said disorders. This trial may be done before the larger trial as a quick and inexpensive method of estimating the effect of an given immunization protocol.

VII. Kits

The present invention also encompasses kits for providing immunogenic agents of the present invention for administration of one or more immunogenic agents according to methods of the present invention. Such kits may provide receptacles of immunogenic agents in forms suitable for pharmacologic administration, as described herein or as could be provided by one skilled in the art based on the teaching and guidance presented herein, without undue experimentation. Preferred examples of such forms for administration are for oral or injection administration. Such kits may include, as non-limiting examples, at least one immunogenic agent comprising an anthrax or plague immunogen and at least one other immunogen corresponding to a different organism and or disease selected from the group consisting of diphtheria, pertussis, measles, mumps, rubella, small pox, pneumococcal, CMV, HIV, meningitis, tetanus, hemophilus influenza, hepatitis B, hepatitis, cholera, varicella, typhoid, yellow fever, neisseria, plague, adenovirus, hepatitis C, herpes, anthrax,plague, malaria, rabies, and/or polio virus immunogen, or a molecule that cross reacts immunologically to the immunogens. Another non-limiting example of such kits includes at least one non-pediatric immunogen and at least pediatric immunogen. Optionally and preferably the kits are in the form of a pharmaceutical composition optionally further comprising a pharmaceutically acceptable carrier, such as a vaccine adjuvant or a depot adjuvant, such as aluminum, calcium or a salt thereof.

Having now generally described the invention, the same will be more readily understood through reference to the following example which is provided by way of illustration, and is not intended to be limiting of the present invention.

EXAMPLES

In Examples 1 and 2 mentioned below, initial vaccinations were either at day 8, 15 or day 1, 3, 10 respectively. This initial schedule was designed to minimize the phenomenon of under immunizing mice due to extravasation of vaccine from their abdomen and inadvertent injection into the visceral organs, bladder and gastrointestinal tract, which results in rapid clearance of the vaccine. Less frequent early administrations are needed for larger mammals when one is sure that extravasation or visceral injection does not occur. After the initial challenge injections every other week or even less frequent suffice.

The method of administration and the compositions contained in this invention allow relatively low amounts of immunogenic agent to be given. The anthrax vaccine, for example, as supplied by the manufacturer contains less than 200 micrograms of protein/ml as calculated using Lawry-based protein determination kit (Sigma, St. Louis, Mo.). Using the dilutions given in Example 1, the amount injected into mice comes to 0.2, 0.6, 0.8 μg protein on day 8, 15, 29. These amounts correspond to roughly 40–60 μg/kg body weight which are pharmaceutically acceptable doses.

The following examples involve immune modulation using commonly available human vaccines: anthrax vaccine, A, (Michigan Department of Health, Lansing, Mich.); combined diphtheria, tetanus vaccine, DT, (Connaught, Swiftwater, Pa.); combined whole cell diphtheria tetanus pertussis vaccine, DTP, (Connaught); and plague vaccine, P, (Miles, West Haven, Conn.). All vaccines are produced from killed microorganisms, and all except the plaque vaccine have an aluminum based adjuvant. The DT vaccine contains purified toxoids while the anthrax and pertussis vaccines are less pure. Vaccines are diluted using sterile technique in sterile phosphate buffer solution pH 7.4 using the notation 1:100 to indicate 1 part vaccine per 100 part PBS by volume. Vaccines were administered by intraperitoneal injections for convenience though other routes would be effective.

It is known that even though vaccines from different manufacturers provided similar protection to an infectious agent different vaccines contain different antigens, and different amounts of similar antigens (Merk Sharp Dome 1991). The following data shows that the exposure to new antigens at 2 months increases the risk of developing diabetes and chronic immune mediated disorders. The epidemiology data shown below demonstrates that different vaccines can interact to decrease the incidence of chronic immune mediated disorders or increase them.

Example 1

The first Example involved injecting anthrax vaccine diluted in PBS into female non-obese diabetic prone (NOD) mice (n=19) (Taconic, Germantown, N.Y.) on day 8 (0.1 ml, 1:100), day 15 (0.15 ml, 1:50), and day 29 (0.2 ml, 1:50) of life. A second group of NOD (n=20) received plaque vaccine diluted in PBS on the same days but at a slightly lower dilution, day 8 (0.1 ml, 1:50), day 15 (0.15 ml, 1:50), and day 29 (0.2 ml, 1:25). A third group of NOD (n=20) received a similar volume of PBS control on the same days as the mice in the first two groups.

Starting at approximately 16 weeks and continuing every 2 weeks until 28 weeks, tail blood was removed and checked for glucose using glucose sensitive chemstrips (Boehringer Mannheim, Indianapolis, Ind.). A blood glucose level over 300 mg/dl was considered positive. The cumulative incidence of diabetes in the anthrax treated group flattened out at 42.1% with no new cases detected after 24 weeks. The group receiving the plague vaccine appeared to begin flattening out and reached a cumulative incidence of 57.9% diabetic at 28 weeks. The PBS control group, showed a continual increase in the cumulative incidence of diabetes from 30% at 16 weeks to 65% at 28 weeks (FIG. 1). The remaining anthrax treated animals and PBS controls in experiment 1 were bled at 36 weeks. The net result was that no new cases of diabetes were detected in the anthrax treated group from 24 to 36 weeks and the cumulative incidence of diabetes flattened out at 42.1% compared to an incidence of 75% at 36 weeks in the PBS treated animals (FIG. 1). The flattening of cumulative incidence of diabetes curve indicates that diabetes is prevented not just delayed.

Example 2

A second set of experiments was designed to see if the therapeutic potential of anthrax vaccine could be improved by adding additional agents and changing the dosing schedule. Anthrax vaccine was given alone, with the combined diphtheria tetanus vaccine, or with the combined whole cell pertussis diphtheria tetanus vaccine. A series of nine intraperitoneal injections of the vaccines diluted in PBS were given to newborn NOD female mice using the following protocol: day 1 (0.1 ml, 1:100), day 3 (0.1 ml, 1:100), day 10 (0.15 ml, 1:100 ml), week 4 and every 2 weeks through week 14 (0.2 ml, 1:50). Vaccines were mixed prior to injection so volume in the notation refers to total volume injected.

Two control groups were used for Example 2. The first control involved injecting PBS using the dosing protocol mentioned above. The second control group in Example 2 received a single intraperitoneal injection of whole cell DTP vaccine diluted in PBS (0.2 ml, 1:50) at 2 months of age. This group was designed to see if the current immunization schedule of humans could inhibit the development of diabetes.

Figure 2:
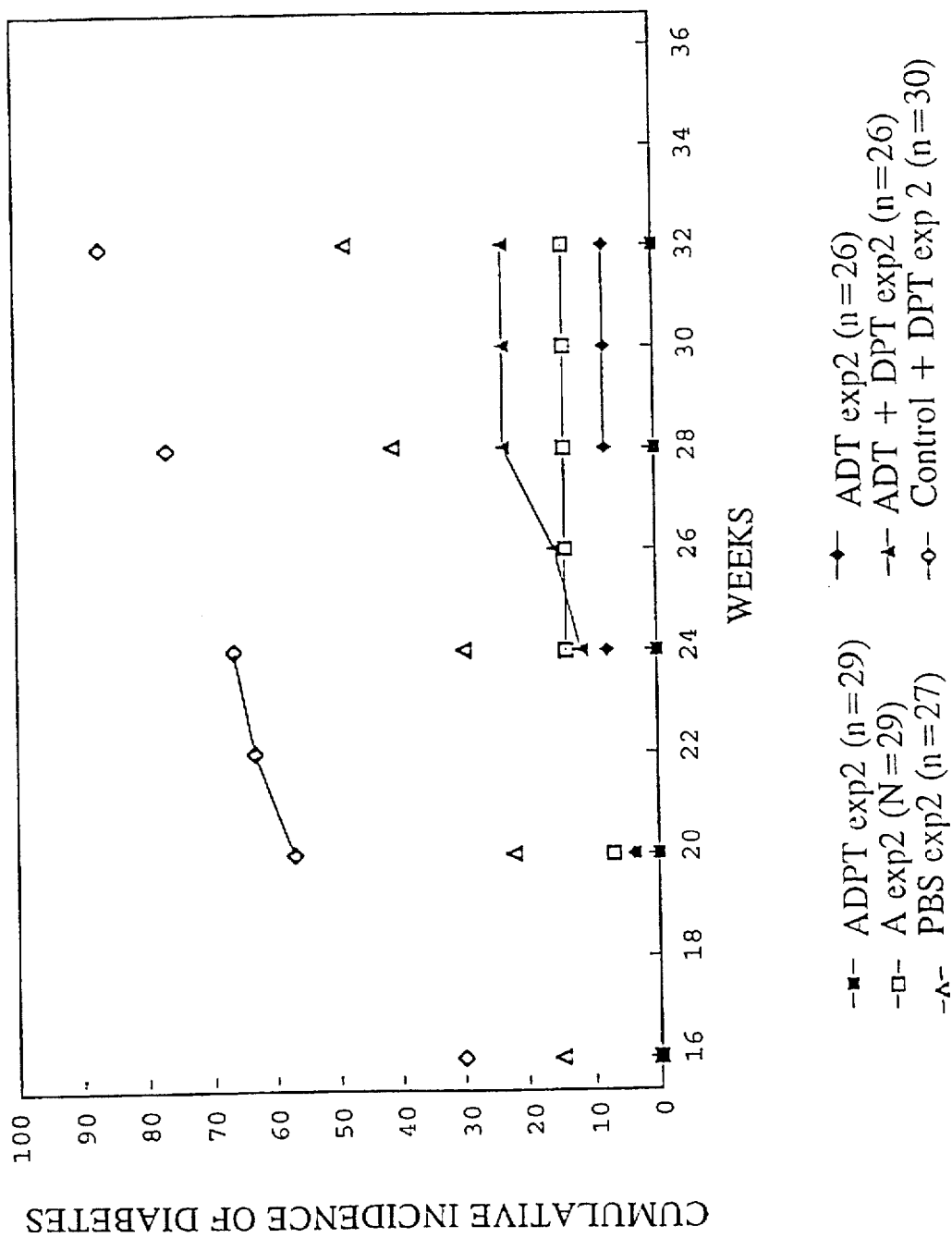
FIG. 2 depicts data from Example 2. Animals were given 1 of 6 treatments: anthrax and the whole cell DTP vaccine (ADPT exp2); anthrax and the diphtheria tetanus vaccine (ADT exp2); anthrax vaccine alone (A exp2); a single injection of DTP vaccine at week 8 (control+DPT exp2); anthrax and the diphtheria tetanus vaccine with the whole cell DTP vaccine substituted for the diphtheria tetanus vaccine at 8 weeks (ADT+DPT exp2); and PBS control (PBS exp2). Data show a single injection of DTP does not prevent diabetes and actually increases the incidence of diabetes as seen in the difference between the group receiving ADT+DTP and ADT. All of the animals in the group receiving ADTP did not develop diabetes.

The new dosing schedule used in Example 2 greatly reduced development of diabetes in the NOD mice. The group receiving anthrax vaccine alone (n=29) had a cumulative incidence of diabetes that peaked at 24 weeks and remained constant at 13.8% through the 32nd week. These results compare to a cumulative incidence of 42.1% in the group receiving anthrax vaccine in Example 1. The most remarkable results in Example 2 occurred with animals treated with anthrax vaccine combined with the whole cell pertussis, diphtheria and tetanus vaccine. None of 29 animals developed diabetes by 32 weeks of age (FIG. 2).

The addition of the combined diphtheria and tetanus vaccine mixed with anthrax inhibited diabetes to a greater extent than anthrax alone but less than the combination of anthrax and DTP. only 7.7% of animals receiving A+DT (n=26) developed diabetes by 32 weeks. A second group of mice (n=26) received a similar treatment of A+DT but were injected with DTP vaccine in place of DT at week 8. This was done to simulate the normal immunization of humans at 2 months with DTP. The animals in the later group developed a higher cumulative incidence of diabetes than those who did not receive pertussis component at 8 weeks, 23% versus 7.7% respectively at 32 weeks.

The injection of PBS slowed the progression of diabetes but the cumulative incidence curve did not flatten out during the 32 week study. The cumulative incidence in the PBS control was 48.1% at 32 weeks compared to 65% at 28 weeks in the PBS control of Example 1. The increased suppression of diabetes in the Example 2 group may be due to inflammation in the abdomen caused by the earlier and more frequent injections.

The control group receiving 1 injection of DTP at 8 weeks, developed a cumulative incidence of diabetes of 86.7% at 32 weeks. While the normal childhood vaccination schedule recommends a second injection at 16 weeks, 30% of animals already had diseases by this time and many of the rest probably had significant subclinical disease. A second injection would not have prevented disease in at least 30% of animals and thus the data clearly shows the current childhood immunization schedule for humans is ineffective in preventing immune mediated disorders.

Example 3

Another experiment involved injecting newborn mice with 15 mg/kg/day of cyclosporine (Sandoz, East Hanover, N.J.) intraperitoneally for the first 7 days of life to make the animals prone to developing autoimmunity (Sakaguchi and Sakaguchi 1989). Female C3H/Hen mice (Harlan Sprague Dawley, Indianapolis, Ind.) were then injected with a combination of the anthrax vaccine and the DT vaccine, or PBS control starting several days later to see if the vaccine would prevent the development of autoimmunity. The injection schedule was as folows: day 10 (0.15 ml, 1:100), day 17 (0.2 ml, 1:50) and every 2 weeks for 2 more injections (0.2 ml, 1:50).

A second injection schedule was performed using anthrax vaccine mixed with DTP vaccine to determine if the effect derived from the first set of experiments could be magnified by including pertussis vaccine at higher doses. injections were as follows: day 6–8 (0.15 ml, 1:10), day 14–16 (0.2 ml, 1:10) and Day 27–29 (0.2 ml, 1:10), where the notation 6–8 means one administration during the period of 6 to 8 days.

Tail blood was drawn from mice at the age of about 8 weeks and the resulting sera, diluted 1:80 in a solution containing PBS and 3% fetal calf serum, was screened for autoantibodies using ELISA assays against gastric antigens (Sakaguchi and Sakaguchi 1989). The microsomal antigens were plated on Immulon 3 (Dynatech Laboratories, Chantilly, Va.). A second ELISA assay was prepared similarly by plating optimal amounts of $E.\ coli$ DNA (Sigma, St. Louis, Mo.) on immulon 3 plates. An alkaline phosphatase-conjugated anti-IgG Fc fraction (Jackson Immunoresearch, West Grove Pa.) was used as the secondary antibody and the substrate was a $2 \times 10^{-4}$M 4-Methyumbelliferyl phosphate solution (Classen and Shevach, 1991). Plates were read on a Dynatech MicroFLOUR machine which uses a 365 nm Broadband Filter for the excitation beam and 450 nm narrow band interference filter for the emission beam.

Of those receiving the ADT treatment 22% n=23) were free of antigastric antibodies compared to 12% (n=25 of female mice which received the PBS control. One control animal had DNA antibodies compared to none of the ADT treated mice. The effect was significantly greater in those mice receiving anthrax vaccine and DTP, as 61% (n=23 males and females) did not develop antigastric antibodies. Methods and compositions of the present invention are thus effective in preventing or substantially reducing the incidence of several chronic immune mediated disorders.

Example 4

An epidemiology study was performed, to verify that immunization practices with pharmaceutically acceptable doses of pharmaceutically acceptable vaccines modulates the development of diabetes. The study made the following assumptions. Western nations included in the study had developed comparable quality of health care allowing for similar risk of neonatal infections and similar efficiency in diagnosing diabetes. Pharmaceuticals were produced using a similar high quality, GMP. The amount of diphtheria and tetanus toxoid given to people in different countries did not induce a significant biological difference. Epidemics traveled freely across borders such that a person in a given western developed nation was as likely to be exposed to a given pathogen as some one in another country.

Eastern European countries were excluded from this study for several reasons. Health care is below western standards leading to a risk of under diagnosing the incidence of diabetes and an increased incidence of neonatal infections which could decrease the incidence of diabetes. Vaccines often lack the quality control seen in products from the west. Accurate estimates of vaccination and revaccination rates are often lacking.

Sweden was one country that was difficult to characterize. The country stopped immunizing newborns with BCG in the middle of 1975 but the date it stopped revaccinating school children is less clear. Pertussis vaccination of newborns was stopped in 1979. Data on immunization practices from Belgium and Sardinia were not available at time of analysis. These changes are expected to decrease the incidence of diabetes in people in Sweden in the coming years.

Data on the incidence of diabetes was taken from the following multiple sources. (Green et al 1992; Nystrom, Dahlquist, Rewers, Wall 1990; Helgason, Danielsen, and Thorsson 1992; Metcalfe and Baum 1991; Levy-Marshal et al. 1990; Tuomilehto et al 1991.) Immunization practices in each country were taken from an assortment of publications.

The data in Table I shows that the incidence of diabetes mellitus, ages 0–14, in a western european country correlates very well with the use of BCG and pertussis vaccines. The use of pertussis vaccine increases the incidence of diabetes from 6.65/100K in people that do not receive either BCG or pertussis to approximately 10.8/100K in people who receive pertussis vaccine but not BCG. An early immune challenge, in this case BCG, decreases the incidence of diabetes in people who receive pertussis vaccine from 10.8 to 7.4/100K. A strong immune response later in life, BCG for example, causes almost a doubling in the incidence of diabetes from 10.5/100K in those who received pertussis vaccine to 10.8 to 9.6/100K in those who received pertussis vaccine and a primary BCG vaccination during school age. Those who received an childhood vaccination program of neonatal BCG and pertussis vaccination along with revaccination of BCG during school age had an even higher incidence of diabetes, 29/100K, presumably due to an even higher immune response to BCG.

Epidemiology data in the U.K. supports the animal data that vaccination with DTP induces diabetes. During the pertussis scare of the 70's and early 80's England had a significantly lower immunization rate for pertussis than Scotland. This can explain the lower incidence of diabetes in England than Scotland in 1988. Furthermore in Scotland those from deprived neighborhoods received fewer vaccinations which could explain the lower incidence of diabetes in areas of deprivation. (Metcalfe and Baum 1991; Patterson and Waugh 1992; Wrench, McWhirter, and Pearson 1991; Maclure and Stewart 1984).

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Any description of a class or range as being useful or preferred in the practice of the invention shall be deemed a description of any subclass or subrange contained therein, as well as a separate description of each individual member or value in said class or range.

TABLE I

| Vaccination Trends Age 0–14 Years. | |
|---|---|
| No Pertussis, No BCG (6.65 avg) | |
| Italy (mainland) | 1988 (6.65) |
| Pertussis, BCG Birth (7.4 avg) | |
| Republic of Ireland | 1988 (6.8) |
| France | 1988 (7.8) |
| Austria | 1988 (7.7) |
| Pertussis, No BCG (10.8 avg) | |
| Iceland | 1980–1989 (10.8) |
| Netherlands | 1988 (11.0) |
| Catelina | 1988 (10.6) |
| Pertussis, BCG Vaccination School Age (19.6 avg) | |
| England | 1988 (16.4) |
| Scotland | 1988 (19.8) |
| Denmark | 1988 (21.5) |
| Norway | 1988 (20.8) |
| Pertussis, BCG Birth + Revaccination School Age (29.6 avg) | |
| Finland | 1988 (34.3) |
| Sweden | 1987 (25) |

References:

Agnese, di Sant, P.A. (1950) *Amer. J. Publ. Hlth.* 40:674–680.

Blom L., et al (1991) *Diabetologia* 34:176–181.

Classen and Shevach (1991) *Transplantation* 51:1052–1057.

Elias et al (1990) *Proc. Natl. Acado Sci. USA* 87:1576–1580.

Fagan et al (1991) *Diabetes* 40:715–725.

Grange et al (1990) *Tubercle* 71:61–64.

Green A., et al (1992) *Lancet* 339:905–909.

Guberski et al (1991) *Science* 254:1010–1013.

Halsey et al (1985), *Bulletin World Health Org.* 63:1151–1169.

Halsey et al (1985) *New Engl. J. Med.* 313:544–549.

Harada et al (1990) *Diabetes Res. and Clin. Prac.* 8:85–90.

Helgason T., et al (1992) *Diabetolgia* 35:880–883.

Hems et al (1971) *Lancet* 1:183.

Huang et al (1984) *Pediatric Res.* 18(2):221–226.

Huang et al (1991) *Autoimmunity* 9:311–317.

Kojima A. and Prehn RT (1981) *Immunogenetics* 14:15–27. Kdb, H. et al., (1987) *Diabetes Res.* 6:21–27.

Levy-Marshal C., et al (1990) *Diabetologia* 33:465–469.

Maclure A. and Stewart GT (1984) *Lancet September* 22, 682–685.

Merk Sharp Dome (1991) Package insert Recombivax HB. September 1991

Metcalfe MA and Baum JD (1991) *British Medical Journal* 302:443–7.

MMWR 1992. 41, RR-1:1–10

Niskanen L. et al (1991) *Diabetologia* 34:402–408.

Nystrom L. et al (1990) *International J. of Epidemiology* 19:141–146.

Oldstone (1988) *Science* 239:500–502.

Oldstone et al (1990) *J. Exp. Med.* 171:2077–2089.

Patterson CC and Waugh NR (1992) *International J. Epidemiology* 21:108–117.

Pearce et al (1991) *J. Pharmacol. Exp. Therap.* 258:710–715.

Reich et al (1989) *Diabetes* 38:1647–1651.

Sadelain et al (1990) *Diabetes* 39:583–589.

Sakaguchi et al (1989) *J. Immunol.* 142:471–480.

Salonen et al (1975) *Int. J. Cancer* 15:941–946.

Satoh et al (1989) *J. Clin. Invest.* 84:1345–1348.

Sauer, L. W. and Tucker, W. H., (1950) *Amer. J. Publ. Hlth.* 40:681–685.

Serreze et al (1989) *J. Autoimmun.* 2:759–776.

Shintani et al (1990) *J. Immunol.* 144:136–141.

Toyota et al (1978) *Diabetologia* 14:319–323.

Tuomilehto J. et al (1991) *Diabetes Care* 14:982–988.

Wrench J. et al (1991) *British Medical Journal* 302:787–788.

What is claimed is:

1. A method of immunizing a mammal less than 96 months of age against at least one infectious disease, while decreasing the incidence of an autoimmune disease, comprising administering to said mammal one or more pharmaceutically acceptable pharmaceutical preparations, comprising one or more immunogens, according to an immunization schedule according to which, at specific times after birth, the mammal receives one or more pharmaceutically acceptable doses of one or more immunogens;

said mammal thereby receiving, for each said infectious disease, a suitable immmogen in such amounts, given at such ages, as to be effective to substantially prevent or substantially reduce the severity of such infectious disease;

said administering further resulting in an immune response in said mammal sufficient to substantially reduce the incidence of an autoimmune disease in such mammals;

said mammals are selected from the group consisting of humans, and nonhuman mammals which are animal models of a human autoimmune disease, the first dose of said immunization schedule being administered when the mammal is less than 42 days old, measured from birth, where, if only one immunogen is administered according to said immunization schedule, that immunogen is one other than BCG, where, when all of the immunogens administered are selected from the group consisting of BCG, diphtheria, tetanus, whole cell pertussis, polio, hepatitis B, hemophilus influenza, measles, mumps and rubella immunogens, at least one of the following conditions applies: (a) immunogens are administered on at least three different dates prior to 42 days after birth, or (b) immunogens are administered on at least three different dates, and the maximum interval between administrations is about two weeks, or less, where said autoimmune disease is selected from the group consisting of diabetes mellitis and systemic lupus erythrematosis.

2. The method of claim 1 where said mammal is not immunized with an immunogen in such amounts and at such times as would substantially induce said autoimmune disease.

3. The method of claim 1, wherein at least four doses are administered before 42 days after birth.

4. The method of claim 1, wherein no tolerogen is administered prior to 42 days after birth.

5. The method of claim 1 wherein at least one immunogen other than a diphtheria, tetanus, pertussis, polio, hepatitis B, hemophilus influenza, measles, mumps and rubella immunogen is administered.

6. The method of claim 5 wherein one immunogen other than a BCG, diphtheria, tetanus, pertussis, polio, hepatitis B, hemophilus influenza, measles, mumps and rubella, influenza, cholera, BCG, plague, pneumococcus, neisseria, varicella, rabies, typhoid and yellow fever immunogen is administered.

7. The method of claim 1 wherein for at least one such immunogen, the total dosage during the first 112 days after birth is substantially greater than that required for immunization against the infectious disease with which it is associated.

8. The method of claim 1 where said immunogen is one other than a BCG or smallpox immunogen.

9. The method of claim 1 wherein the first dose is administered before 28 days after birth.

10. The method of claim 1 wherein said immunogens are non-living.

11. The method of claim 1 in which the immunogens are administered parenterally.

12. The method of claim 1 in which the reduction in incidence of the autoimmune disease is at least 10%.

13. The method of claim 1 in which the reduction in incidence of autoimmune disease is at least about 50%.

14. The method of claim 1 in which the reduction in incidence of autoimmune disease is at least about 20%.

15. The method of claim 1 in which said mammal is of a population in which the normal incidence of autoimmune disease is at least 5.8 per 100,000 individuals of 0–14 years of age, said incidence being standardized for age and sex.

16. The method according to claim 1, wherein said diabetes mellitus is decreased.

17. The method according to claim 1, wherein said mammal is a human.

18. The method according to claim 1, wherein at least one of said immunogens is an immunogen selected from the group consisting of an anthrax immunogen, a small pox immunogen, a pneumococcal immunogen, a cholera immunogen, a varicella immunogen, a typhoid immunogen, a yellow fever immunogen, a neisseria immunogen, a plague immunogen, an influenza immunogen, a herpes immunogen, a meningitis immunogen, an adenovirus immunogen, a cytomegalovirus immunogen, a hepatitis C immunogen, rabies and a molecule that cross reacts to any of said immunogens.

19. In a method for immunization against at least three infectious diseases, comprising administering at least one pharmaceutically acceptable dose of diphtheria/tetanus/pertussis vaccine to a mammal of at least 42 days of age, the improvement comprising:

further administering to said mammal at least one pharmaceutically acceptable dose of diphtheria/pertussis/tetanus vaccine, wherein said further administration is according to at least one step selected from the group consisting of (1) administrating at least two doses of said diphtheria/tetanus/pertussis vaccine at less than 42 days of age of said mammal;

(2) administering said at least one of said dose of said diphtheria/tetanus/pertussis vaccine at less than 42 days of age of said mammal and also administering at least a second dose of said diphtheria/tetanus/pertussis vaccine, said second dose or any subsequent dose administered less than 28 days after the preceding dose when said mammal is less than 175 days of age; and (3) administering said at least one dose of said diphtheria/tetanus/pertussis vaccine at less than 42 days of age of said mammal and also administering as a total of at least four doses of said dipheria/tetanus/pertussis vaccine prior to the age of 112 days of said mammal, where in the further administration reduces the incidence of diabetes mellitis in a population and/or subpopulation of said mammals, where said mammal is a human, or an animal model of a human diabetes, and is not a streptozocin-treated mouse, and said mammal receives at least one of the following immunogens prior to age of 24 months: hepatitis B, hemophilus influenza B, mumps, rubella, chicken pox, acellular pertussis, and pneumococcus immunogens.

20. The method of claim 19 wherein said further administration comprises administering to said mammal of at least 28 days of age but less than 175 days of age, at least one pharmaceutically acceptable dose of at least one pharmaceutically acceptable immunogen, wherein said at least one dose comprises a total of at least 4 separate pharmaceutically acceptable doses of at least one pharmaceutically acceptable immunogen from the group consisting of a diphtheria/tetanus/pertussis immunogen, a hepatitis B immunogen, a hemophilus influenza immunogen, a measles/mumps/rubella immunogen, a polio immunogen, and a non-pediatric immunogen, administered to said mammal during said ages, at least 2 of said at least 4 doses provided prior to the age of 112 days of said mammal, and wherein the further administration reduces the incidence of diabetes mellitis in a population and/or subpopulation of said mammals.

21. In a method for immunization against at least two infectious diseases, comprising administering at least one pharmaceutically acceptable dose of diphtheria/tetanus/pertussis vaccine and at least one pharmaceutically acceptable dose of hemophilus influenza vaccine to a mammal of at least 42 days of age, the improvement comprising:

further administering to said mammal at least one pharmaceutically acceptable dose of at least one of a diphtheria/pertussis/tetanus vaccine and a hemophilus influenza vaccine wherein said further administration is according to at least one method from the group consisting of (1) administrating at least one dose of both said diphtheria/pertussis/tetanus vaccine and said hemophilus influenza vaccine at less than 42 days of age of said mammal and at least a second dose of at least one said vaccine prior to 42 days of age of said mammal;

(2) administering at least one of said dose of both said diphtheria/tetanus/pertussis vaccine and said hemophilus influenza vaccine at less than 42 days of age of said mammal and also administering at least a second dose of both of said vaccines, wherein said second dose and or any subsequent dose is administered at less than 42 days after the preceding dose when said mammal is less than 175 days of age; and (3) administering at least one of said dose of both said diphtheria/tetanus/pertussis vaccine and said hemophilus influenza vaccine at less than 42 days of age of said mammal and administrating at least four doses, prior to the age of 112 days, of said mammal for said diphtheria/pertussis/tetanus vaccine or said hemophilus influenza vaccine, the incidence of diabetes mellitis in a population and/or subpopulation of said mammals, where said mammal is a human, or an animal model of a human diabetes, and is not a streptozocin-treated mouse, and said mammal receives at least one of the following immunogens prior to age of 24 months: hepatitis B, hemophilus influenza B, mumps, rubella, chicken pox, acellular pertussis, and pneumococcus immunogens.

22. In a method for immunization against at least two infectious diseases, comprising administering at least one pharmaceutically acceptable first dose of at least one pharmaceutically acceptable immunogen selected from the group consisting of a diphtheria/tetanus/pertussis immunogen, a polio immunogen, a hepatitis B immunogen, a hemophilus influenza immunogen, a non-pediatric immunogen, and a measles/mumps/rubella immunogen, to a mammal after 112 days of age but prior to 724 days of age, the improvement comprising:

further administering to said mammal, prior to the age of 112 days, at least one pharmaceutically acceptable second dose containing a greater amount of said immunogen than the amount of immunogen administered as said first dose after 112 days of age but prior to 724 days of age of said mammal, wherein the further administration reduces the incidence of diabetes mellitis in a population and/or subpopulation of said mammals, where said mammal is a human, or an animal model of a human diabetes, and is not a strepzocin-treated mouse, and said mammal receives at least one of the following immunogens prior to age of 24 months: hepatitis B, hemophilus influenza B, mumps, rubella, chicken pox, acellular pertussis, and pneumococcus immunogens.

23. In a method for immunization against at least two infectious diseases, comprising administering at least one pharmaceutically acceptable dose of a non-whole cell pertussis vaccine to a mammal at least 42 days of age but prior to 724 days of age, the improvement comprising further administering to said mammal at least one pharmaceutically acceptable dose of at least one pharmaceutically acceptable immunogen selected from the group consisting of an diphtheria/tetanus immunogen, a non-whole cell pertussis immunogen, a whole cell pertussis immunogen, a polio immunogen, a hemophilus influenza immunogen, a measles/mumps/rubella immunogen and a non-pediatric immunogen, wherein said further administration is according to at least one selected from the group consisting of (1) administrating said at least one dose of said immunogen at less than 42 days of age of said mammal;

(2) administering said at least one dose of said immunogen, said dose comprising at least a second dose, said second dose or any subsequent said dose administered less than 28 days after the preceding dose when said mammal is less than 175 days of age; and (3) administrating at least four doses prior to the age of 112 days of said mammal, wherein the further administration reduces the incidence of diabetes mellitis in a population and/or subpopulation of said mammals, where said mammal is a human, or an animal model of a human diabetes, and is not a streptozocin-treated mouse, and said mammal receives at least one of the following immunogens prior to age of 24 months: hepatitis B, hemophilus influenza B, mumps rubella, chicken box, acellular pertussis, and pneumococcus immunogens.

24. In a method for immunization against at least two infectious diseases, comprising administering at least one pediatric vaccine to a mammal of at least 42 days of age, the improvement comprising:

further administering to said mammal at least one pharmaceutically acceptable dose of at least one pharmaceutically acceptable vaccine selected from (i) a combined vaccine containing at least diphtheria, tetanus, pertussis, and hemophilus influenza immunogens, and (ii) a combined vaccine containing at least diphtheria, tetanus, pertussis, and hepatitis B immunogens, wherein said further administration is according to at least one step selected from the group consisting of (1) administrating at least of one of said dose of said combined vaccine at less than 42 days of age of said mammal;

(2) administering at least one of said dose of said combined vaccine, said dose comprising at least a second dose, said second dose or any subsequent dose administered less than 28 days after the preceding dose when said mammal is less than 175 days of age; and (3) administrating at least four doses prior to the age of 112 days of said mammal, wherein the further administration reduces the incidence of diabetes mellitis in a population and/or subpopulation of said mammals, where said mammal is a human, or an animal model of a human diabetes, and is not a streptozocin-treated mouse, and said mammal receives at least one of the following immunogens prior to age of 24 months: hepatitis B, hemophilus influenza B, mumps, rubella, chicken pox, acellular pertussis, and pneumococcus immunogens.

25. In a method for pediatric immunization against at least two infectious diseases, comprising administering at least one pharmaceutically acceptable dose of at least one pediatric vaccine to a mammal of at least 42 days of age, the improvement comprising:

further administering to said mammal at least one pharmaceutically acceptable supraimmunogenic dose of at least one pharmaceutically acceptable vaccine prior to the age of 112 days of said mammal, wherein the further administration reduces the incidence of diabetes mellitis in a population and/or subpopulation of said mammals, where said mammal is a human, or an animal model of a human diabetes, and is not a streptozocin-treated mouse, and said mammal receives at least one of the following immunogens prior to age of 24 months: hepatitis B, hemophilus influenza B, mumps, rubella, chicken pox, acellular pertussis, and pneumococcus immunogens.

26. A method according to claim 25, wherein said at least one supraimmunogenic dose comprises at least a second dose, said second dose or any subsequent supraimmunogeic dose is administered less than 28 days after the preceding dose when said mammal is less than 175 days of age.

27. In a method for immunization against at least two infectious diseases, comprising administering at least one pharmaceutically acceptable dose of at least one pediatric vaccine to a mammal of at least 42 days of age, the improvement comprising:

(a) further administering to said mammal at least one pharmaceutically acceptable dose of at least one pharmaceutically acceptable immunogen to said mammal prior to the age of 8 days; and (b) further administering at least one pharmaceutically acceptable dose of at least one pharmaceutically acceptable immunogen to said mammal at least 11 days of age but less than 26 days of age, wherein the further administrations reduce the incidence of diabetes mellitis in a population and/or subpopulation of said mammals, where said mammal is a human, or an animal model of a human diabetes, and is not a streptozocin-treated mouse, and said mammal receives at least one of the following immunogens prior to age of 24 months: hepatitis B, hemophilus influenza B, mumps, rubella, chicken pox, acellular pertussis, and pneumococcus immunogens.

28. The method according to claim 27, further comprising:

(c) additionally administering at least one pharmaceutically acceptable dose of at least one pharmaceutically acceptable immunogen at least 11 days, but less than 26 days, after the last dose of said immunogen preceding 26 days of age of said mammal.

29. The method according to claim 28, further comprising:

(d) administering at least one pharmaceutically acceptable dose of at least one pharmaceutically acceptable immunogen at least 11 days, but less than 26 days, after said additional administaration of step (c).

30. In a method for immunization against at least two infectious diseases, comprising administering at least one pharmaceutically acceptable dose of at least one pharmaceutically acceptable immunogen to a mammal, the improvement comprising:

further administering at least a second separate pharmaceutically acceptable dose of at least one pharmaceutically acceptable immunogen, said second dose and or any subsequent dose is administered less than 28 days after the preceding dose, wherein,(i) said second or any subsequent dose contains the same or different immunogens or the same or different amounts of said immunogens as any other dose; (ii) each said separate dose is administered during a 0–78 hour period, and (iii) the further administration reduces the incidence of diabetes mellitis in a population and or subpopulation of said mammals, where said mammal is a human, or an animal model of a human diabetes, and is not a streptozocin-treated mouse, and said mammal receives at least one of the following immunogens prior to age of 24 months: hepatitis B, hemophilus influenza B, mumps, rubella, chicken pox, acellular pertussis, and pneumococcus immunogens.

31. The method according to claim 30, wherein at least 4 of said separate doses are administered prior to 112 days of age of said mammal.

32. A method of immunizing a mammal less than 96 months of age against at least two infectious diseases and at least one chronic immune-mediated disorder, comprising
administering to said mammal one or more pharmaceutically acceptable pharmaceutical preparations, comprising one or more immunogens, according to an immunization schedule according to which, at specific times after birth, the mammal receives one or more pharmaceutically acceptable doses of one or more immunogens;
said mammal thereby receiving, for each said infectious disease, a suitable immunogen in such amounts, given at such ages, as to be effective to substantially prevent or substantially reduce the severity of such infectious disease;
said administering further resulting in an immune response in said mammal sufficient to substantially reduce the incidence of diabetes mellitis in such mammal;
the first dose of said immunization schedule including an immune modulator beginning 42 days before birth,
where said mammal is not immunized with an immunogen in such amounts and at such times as would substantially induce diabetes mellitis, where said mammal is a human, or an animal model of a human diabetes, and is not a streptozocin-treated mouse, and said mammal receives at least one of the following immunogens prior to age of 24 months: hepatitis B, hemophilus influenza B, mumps, rubella, chicken pox, acellular pertussis, and pneumococcus immunogens.

33. A method of immunizing a mammal less than 24 months of age against at least 2 infectious disease and diabetes mellitus, comprising administering to said mammal one or more pharmaceutically acceptable pharmaceutical preparations, comprising one or more immunogens, according to an immunization schedule according to which, at specific times after birth; the mammal receives one or more pharmaceutically acceptable doses of two or more immunogens;
said mammal thereby receiving, for each said infectious disease, a suitable immunogen in such amounts, given at such ages, as to be effective to substantially prevent or substantially reduce the severity of such infectious disease;
said administering further resulting in an immune response in said mammal sufficient to substantially reduce the incidence of diabetes mellitus in such mammal;
where said mammal is a human, or an animal model of a human diabetes, and is not a streptozocin-treated mouse;
the first dose of at least 2 immunogens are given before 42 days after birth;
and where said mammal receives at least one of the following immunogens: hepatitis B, haemophilus influenza B, mumps, rubella, varicella, acellular pertussis, and pneumococcus immunogen.

34. The method of claim 33 wherein said mammal is a human.

35. The method of claim 33 wherein said mammal is not immunized with an immunogen in such amounts and at such times as would increase the incidence of diabetes mellitus.

36. The method of claim 33 wherein said 2 immunogens are ones other than a BCG or Hepatitis B immunogen.

37. The method of claim 33 wherein more than 2 doses of at least one said immunogen is given prior to 42 days after birth.

38. The method of claim 33 wherein the longest interval between doses is less than 28 days.

39. The method of claim 33 wherein the first dose is given prior to 15 days after birth.

40. In a method for immunization against at least two infectious diseases, comprising administering at least one pharmaceutically acceptable dose of a conjugated pneumococcal or varicella vaccine to a mammal at least 42 days of age but prior to 724 days of age, the improvement comprising:
further administering to said mammal at least one pharmaceutically acceptable dose of at least one pharmaceutically acceptable immunogen selected from the group consisting of a diphtheria tetanus immunogen, a non-whole cell pertussis immunogen, a whole cell pertussis immunogen, a polio immunogen, a hemophilus influenza immunogen, a measles mumps rubella, varicella, pneumococcal and a non-pediatric immunogen, wherein said further administration is according to at least one selected from the group consisting of
(1) administrating said at least one dose of said immunogen at less than 42 days of age of said mammal;
(2) administering said at least one dose of said immunogen, said dose comprising at least a second dose, said second dose or any subsequent said dose administered less than 28 days after the preceding dose when said mammal is less than 175 days of age; and
(3) administrating at least four doses prior to the age of 112 days of said mammal, wherein the further administration reduces the incidence of diabetes mellitus in a population and/or subpopulation of said mammals.

41. A method of decreasing the incidence of an autoimmune disease which comprises:
administering to said mammal one or more pharmaceutically acceptable pharmaceutical preparations, comprising one or more immunogens, according to an immunization schedule according to which, at specific times after birth, the mammal receives one or more pharmaceutically acceptable doses of one or more immunogens;
said administering resulting in an immune response in said mammal sufficient to substantially reduce the incidence of an autoimmune disease in such mammals;
said mammals are selected from the group consisting of humans, and nonhuman mammals which are animal models of a human autoimmune disease, the first dose of said immunization schedule being administered when the mammal is less than 42 days old, measured from birth, where, if only one immunogen is administered according to said immunization schedule, that immunogen is one other than BCG, where, when all of the immunogens administered are selected from the group consisting of BCG, diphtheria, tetanus, whole cell pertussis, polio, hepatitis B, hemophilus influenza, measles, mumps and rubella immunogens, at least one of the following conditions applies: (a) immunogens are administered on at least three different dates prior to 42 days after birth, or (b) immunogens are administered on at least three different dates, and the maximum interval between administrations is about two weeks, or less, where said autoimmune disease is selected from the group consisting of diabetes mellitis and systemic lupus erythrematosis.

42. The method according to claim 41, wherein at least one of said immunogens is an immunogen selected from the group consisting of an anthrax immunogen, a small pox immunogen, a pneumococcal immunogen, a cholera immunogen, a varicella immunogen, a typhoid immunogen, a yellow fever immunogen, a neisseria immunogen, a plague immunogen, an influenza immunogen, a herpes immunogen, a meningitis immunogen, an adenovirus immunogen, a malaria immunogen, an HIV immunogen, a cytomegalovirus immunogen, a hepatitis C immunogen, a rabies immunogen and a molecule that cross reacts to any of said immunogens.

* * * * *